United States Patent [19]

Sakaguchi et al.

[11] Patent Number: 4,555,470
[45] Date of Patent: Nov. 26, 1985

[54] HEAT-DEVELOPABLE COLOR PHOTOGRAPHIC MATERIAL WITH HEAT FUSIBLE COMPOUND

[75] Inventors: Yukihiko Sakaguchi; Kozo Sato; Hideki Naito; Hiroshi Hara, all of Kanagawa, Japan

[73] Assignee: Fuji Photo Film Co., Ltd., Kanagawa, Japan

[21] Appl. No.: 548,190

[22] Filed: Nov. 2, 1983

[30] Foreign Application Priority Data

Nov. 2, 1982 [JP] Japan .................. 57-193080

[51] Int. Cl.⁴ .................... G03C 1/40; G03C 5/54
[52] U.S. Cl. ..................... 430/203; 430/222; 430/351; 430/559; 430/617; 430/619; 430/562
[58] Field of Search .............. 430/203, 216, 218, 223, 430/372, 551, 351, 617, 619, 607, 222, 559, 562

[56] References Cited

U.S. PATENT DOCUMENTS

| 4,228,235 | 10/1980 | Okonogi et al. | 430/551 |
| 4,308,328 | 12/1981 | Salyer et al. | 430/551 |
| 4,430,415 | 2/1984 | Aono et al. | 430/353 |

FOREIGN PATENT DOCUMENTS 0066282 12/1982 European Pat. Off. ............ 430/203

*Primary Examiner*—Richard L. Schilling
*Attorney, Agent, or Firm*—Sughrue, Mion, Zinn, Macpeak & Seas

[57] ABSTRACT

A heat-developable color photographic material comprising a support having thereon at least a light-sensitive silver halide, a hydrophilic binder, a dye releasing redox compound and a heat fusible compound which has a melting point of 60° C. or higher and is represented by the following general formula (I), (II) or (III):

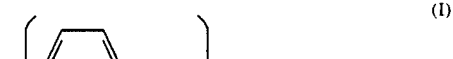

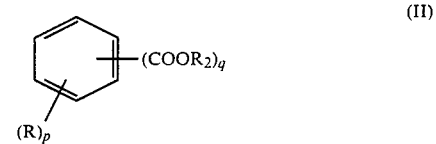

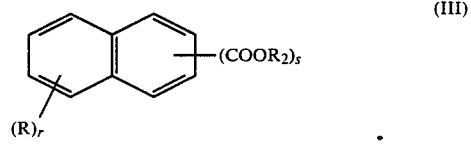

wherein m represents an integer from 1 to 3; n represents an integer from 1 to 8; q represents an integer from 1 to 4; p represents an integer which meets the requirement for $p+g=6$; s represents an integer from 1 to 4; r represents an integer which meets the requirement for $r+s=8$; R represents a hydrogen atom or a substituent as set forth in the specification, and when m, p or r represents 2 or more, R may be the same or different; $R_1$ represents an organic group in $R_1$-$(OH)_n$ which is an alcohol, a phenol or a naphthol each having one or more hydroxy group and includes a saccharide; and $R_2$ represents an organic group in $R_2$-OH which is an alcohol, a phenol or a naphthol.

The heat-developable color photographic material has improved stability during storage before imagewise exposure and the occurrence of fog and the change in the maximum density therein are minimized.

19 Claims, No Drawings

HEAT-DEVELOPABLE COLOR PHOTOGRAPHIC MATERIAL WITH HEAT FUSIBLE COMPOUND

FIELD OF THE INVENTION

The present invention relates to a heat-developable color photographic material containing a heat fusible compound having a melting point of 60° C. or higher.

BACKGROUND OF THE INVENTION

Heat-developable photographic materials are known in the field of these techniques. Heat-developable photographic materials and processes therefor have been described in U.S. Pat. Nos. 3,152,904, 3,301,678, 3,392,020 and 3,457,075, British Pat. Nos. 1,131,108 and 1,167,777, and *Research Disclosure*, No. 17029, pages 9 to 15 (June, 1978).

Many different processes for obtaining color images have been proposed. The formation or bleach of dyes is performed in various processes and includes, for example, the following processes:

(1) formation of a dye by bonding of an oxidized product of a reducing agent which is formed upon the oxidation-reduction reaction between an organic silver salt oxidizing agent and a reducing agent with a coupler.

(2) releasing of a diffusible dye by the reaction of a coupler having a diffusible dye as a releasable group with the oxidized product of a reducing agent described above.

(3) releasing of a diffusible dye by the oxidation-reduction reaction between a silver salt of silver salt forming dye and a reducing agent.

(4) formation of a dye by the oxidatio-reduction reaction between a leuco body of a dye or a precursor thereof and an organic silver salt oxidizing agent.

(5) bleaching of a dye with a metal silver.

(6) releasing of a diffusible dye by the oxidation-reduction reaction between an organic silver salt oxidizing agent and a dye releasing redox compound and the subsequent attack with a nucleophilic agent.

The process of (1) is described, for example, in U.S. Pat. Nos. 3,531,286, 3,761,270 and 4,021,240, Belgian Pat. No. 802,519, *Research Disclosure*, Vol. 139, No. 13946.

The process of (2) is described, for example, in Japanese Patent Application Nos. 71234/81, 93533/81 and 177611/81.

The process of (3) is described, for example, in *Research Disclosure*, Vol. 169, No. 16966.

The process of (4) is described, for example, in U.S. Pat. Nos. 3,985,565 and 4,022,617.

The process of (5) is described, for example, in *Research Disclosure*, Vol. 144, No. 14433, ibid., Vol. 152, No. 15227, U.S. Pat. No. 4,235,957.

The process of (6) is described, for example, in Japanese Patent Application Nos. 65391/81, 84164/81 and 157798/81.

The heat fusible compound according to the present invention is employed in the process of (6).

In the process of (6), an oxidation-reduction reaction occurs between a light-sensitive silver halide and a dye releasing redox compound in the exposed area and subsequently the oxidized product of the dye releasing redox compound is subjected to attack with a nucleophilic agent to release a dye. The dye released in diffusion-transferred into an image-receiving sheet and thus a color image is obtained.

However, the photographic material employed has a disadvantage that stability during preservation is poor and it is difficult to obtain a clear image. The stability during preservation used herein means stability of the photographic material during preservation before heat-development processing. That is, the photographic material has a drawback that the reaction for releasing a dye occurs during preservation thereof before heat-development processing and consequently, fog density and the maximum density are increased in an image obtained by the heat-development processing.

SUMMARY OF THE INVENTION

An object of the present invention is to provide a method for improving the stability during preservation of a heat-developable color photographic material.

Another object of the present invention is to provide a method for restraining the occurrence of fog and the change in the maximum density during preservation of a heat-developable color photoraphic material before heat-development processing.

These and other objects of the present invention will become more apparent from the following detailed description and examples.

These objects of the present invention are attained by a heat-developable color photographic material comprising a support having thereon at least a light-sensitive silver halide, a hydrophilic binder, a dye releasing redox compound and a heat fusible compound which has a melting point of 60° C. or higher and is represented by the following general formula (I), (II) or (III):

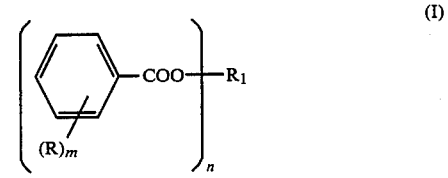

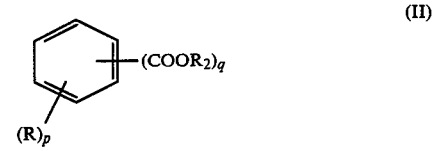

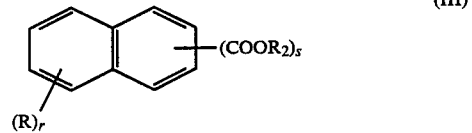

wherein m represents an integer from 1 to 3; n represents an integer from 1 to 8; q represents an integer from 1 to 4; p represents an integer which meets the requirement for $p+q=6$; s represents an integer from 1 to 4; r represents an integer which meets the requirement for $r+s=8$; R represents a hydrogen atom or a substituent selected from an alkyl group, a cycloalkyl group, an aryl group, an alkoxy group, an aryloxy group, an aralkyl group, an acyl group, an acylamino group, an alkylsulfonylamino group, an arylsulfonylamino group, an alkoxyalkyl group, an aryloxyalkyl group, an acyloxy group, an acyloxyalkyl group, a carbamoyl group, a N-substituted carbamoyl group, a ureido group, a N- substituted ureido group, an alkylamino group, a dialkylamino group, an arylamino group, a halogen atom, a hydroxy group, a carboxy group, a nitro group, a cyano group, an alkoxycarbonyl group, an aryloxycarbonyl group and a cycloalkyloxycarbonyl group and the alkyl moiety, the cycloalkyl moiety and the aryl moiety of the substituents may be further substitued with a halogen atom, a hydroxy group, an alkoxy group, a cyano group, an aryloxy group, an alkyl group, an alkoxycarbonyl group or an aryloxycarbonyl group, and when m, p or r represents 2 or more, R may be the same or different; $R_1$ represents an organic group in $R_1-(OH)_n$ which is an alcohol, a phenol or a naphthol each having one or more hydroxy group and includes a saccharide; and $R_2$ represents an organic group in $R_2-OH$ which is an alcohol, a phenol or a naphthol.

DETAILED DESCRIPTION OF THE INVENTION

Preferred examples of the organic groups represented by $R_1$ include those represented by the general formula (IV), (V) or (VI) set forth below in the form of $R_1-(OH)_n$.

$$R_3-(OH)_t \quad \text{(IV)}$$

$$HO-(R_4O)_u-H \quad \text{(V)}$$

$$R_5-[(O)_v-(CH_2)_w-OH]_t \quad \text{(VI)}$$

wherein $R_3$ represents a t valent residue of an alkyl group, a substituted alkyl group, a cycloalkyl group or a substituted cycloalkyl group; $R_4$ represents an alkylene group or a substituted alkylene group; $R_5$ represents a t valent residue of an aryl group or a substituted aryl group; t represents an integer from 1 to 4; u represents an integer from 1 to 3; v represents 0 or an integer of 1; and w represents 0 or an integer from 1 to 3.

Of the compounds represented by the general formula (IV), those represented by the general formula (VII) below are preferred

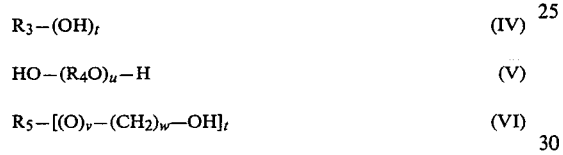

wherein $R_6$, $R_7$ and $R_8$, which may be the same or different, each represents a hydrogen atom, a hydroxy group, a hydroxymethyl group, or an alkyl group having from 1 to 4 carbon atoms; and $R_9$ represents a hydroxy group or a hydroxymethyl group.

Preferred examples of saccharides represented by the general formula (V) include a monosaccharide such as glucose, arabinose, ribose, deoxyribose, xylose, fructose, mannose, galactose, etc. and a disaccharide such as saccharose, lactose, maltose, etc.

Preferred examples of the organic groups represented by $R_2$ in the general formulae (II) and (III) include a phenyl group, a substituted phenyl group, an alkyl group, a substituted alkyl group, a cycloalkyl group and a substituted cycloalkyl group.

Preferred examples of substituents in the substituted aryl group represented by $R_5$ include a hydroxy group, a halogen atom, an alkoxy group, an alkyl group, etc.

Specific examples of the heat fusible compounds suitable for use in the present invention are set forth below, but the present invention is not to be construed as being limited thereto.

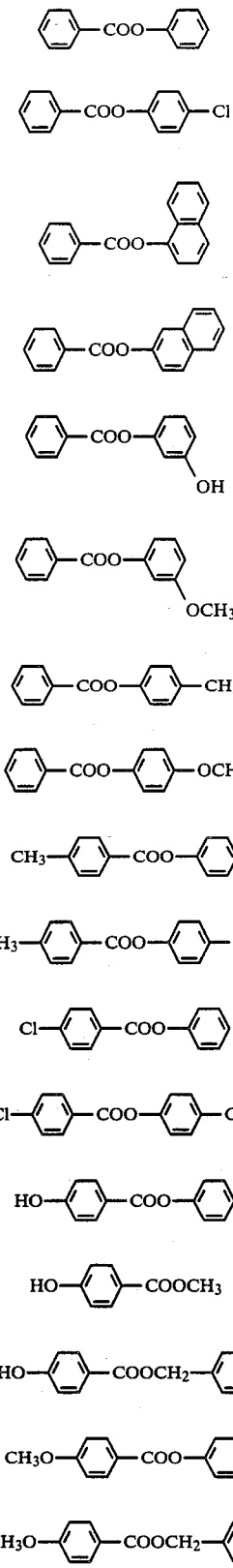

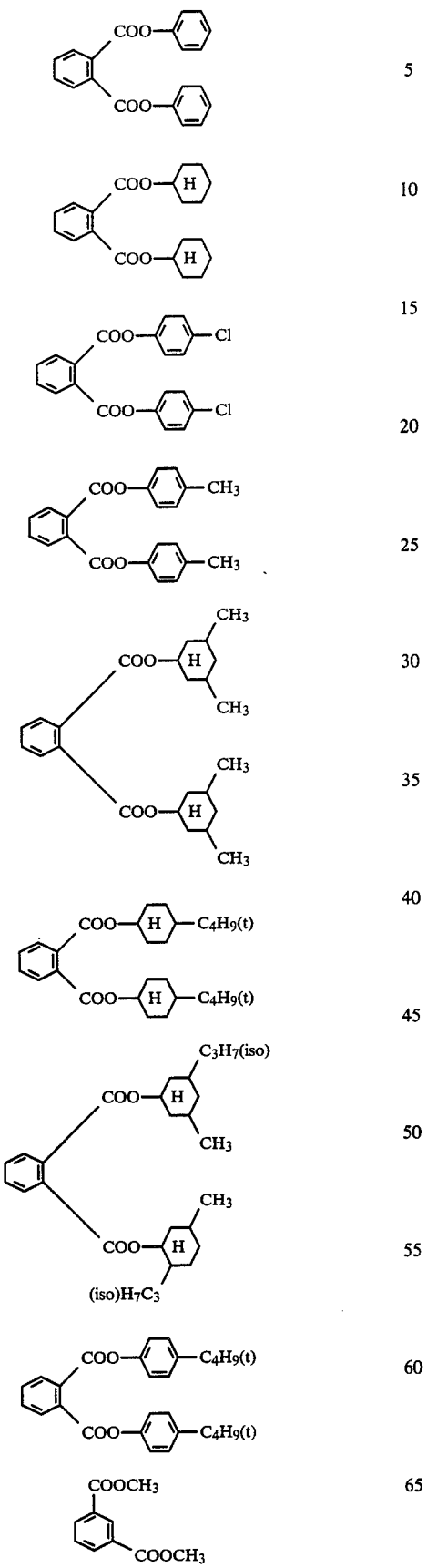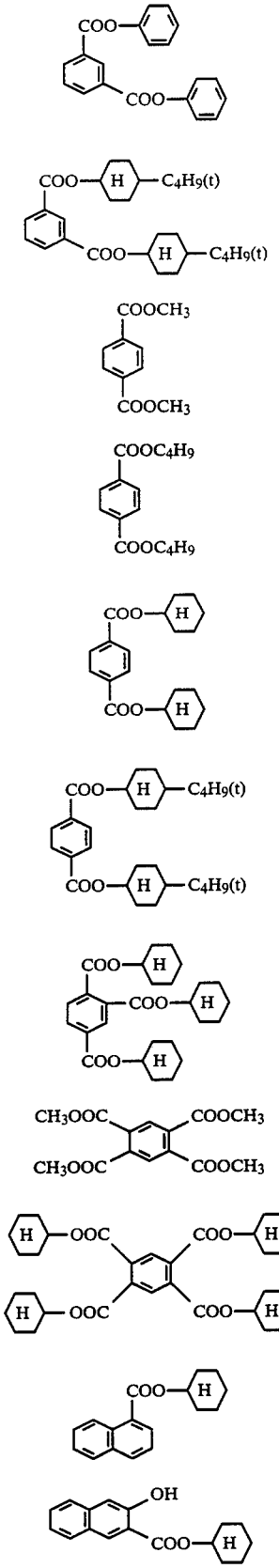

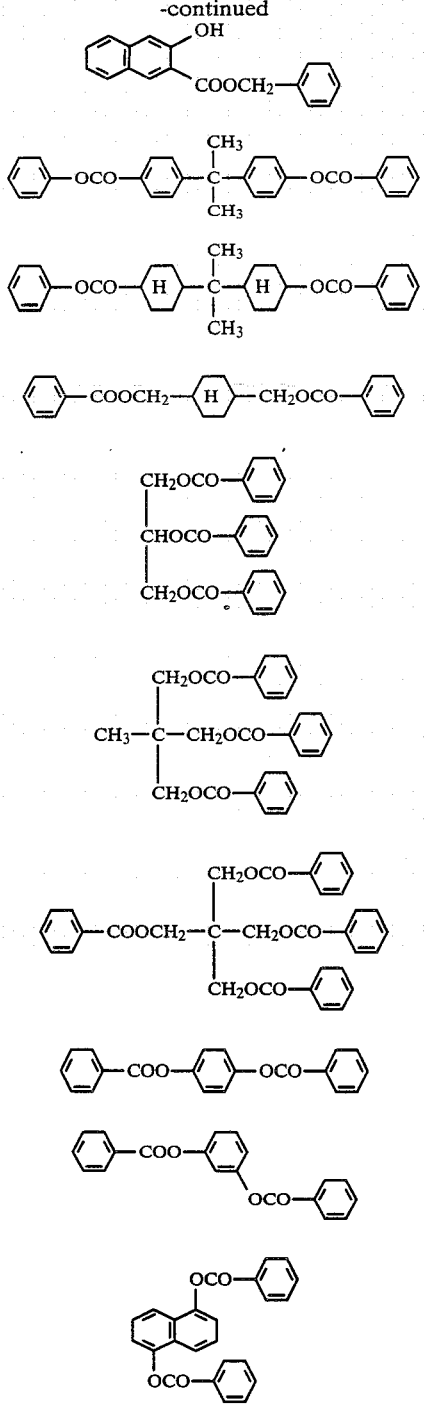

Tetrabenzoylglucose
Pentabenzoylglucose
Hexabenzoylsaccharose
Heptabenzoylsaccharose The heat fusible compounds suitble for use in the present invention are those which are present in a solid state or a near solid and non-fluid state and prevent the redox reaction between silver halide and a dye releasing redox compound or the subsequent dye releasing reaction before heat development, but which become fluid and act as a medium for smoothly carrying out the above described reactions. Therefore, it is desirable that they have an appropriate melting temperature. Compounds having a melting point generally in a range from 60° C. to 200° C., and preferably in a range from 60° C. to 150° C. provide good results.

Preferred examples of the heat fusible compounds according to the present invention are set forth below.

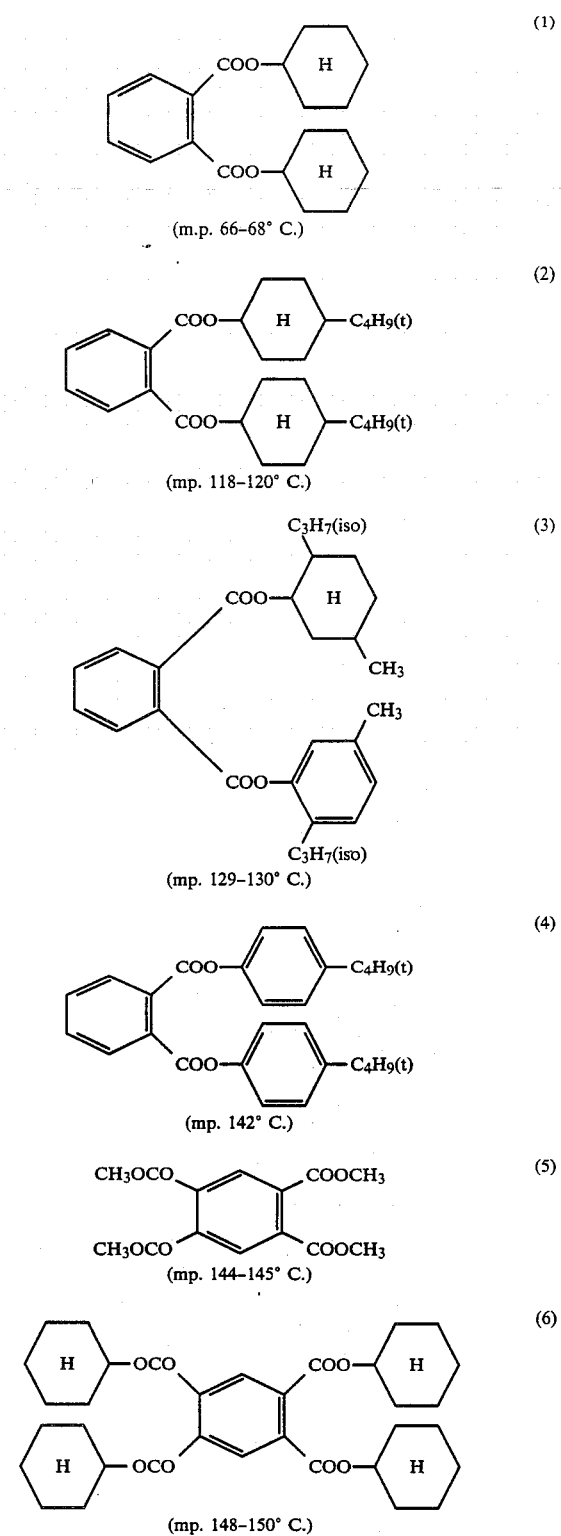

-continued (7)
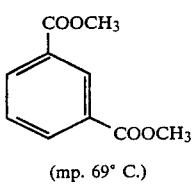
(mp. 69° C.)

(8)
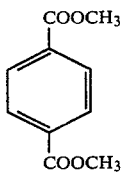
(mp. 142° C.)

(9)
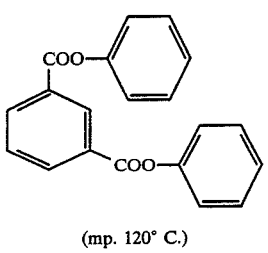
(mp. 120° C.)

(10)
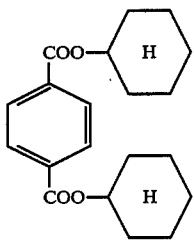
(mp. 75–80° C.)

(11)
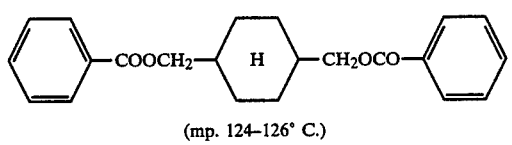
(mp. 124–126° C.)

(12)
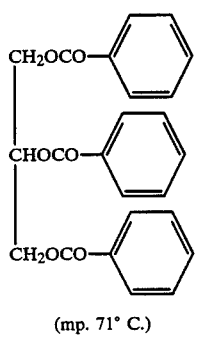
(mp. 71° C.)

-continued

(13)
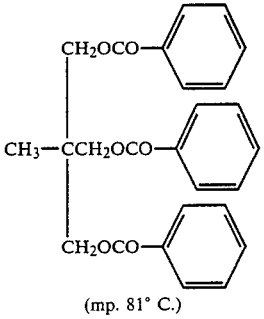
(mp. 81° C.)

(14)
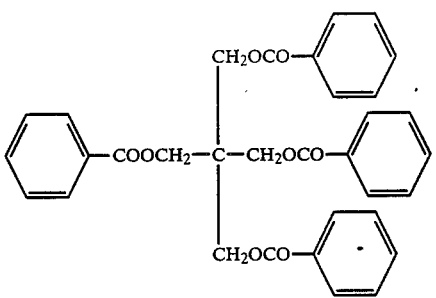
(mp. 99° C.)

Tetrabenzoylglucose (15)
(mp. 119–120° C.)
Heptabenzoylsaccharose (16)
(mp. 98° C.)

The heat fusible compounds according to the present invention can be synthesized by various methods. General methods for syntheses of esters as described, for example, in Shin-Jikken Kagaku Koza, Vol. 14(II), page 1000 (Maruzen, 1977L), Organic Functional Group Preparations, page 245 (Academic Press, 1968), etc. may be applied to, but a method in which an acid chloride of the corresponding benzoic acid derivative and an alcohol or a phenol are subjected to condensation in the presence of a base is easy and provides good results with respect to the heat fusible compounds according to the present invention. Synthesis method of Compound (14) is set forth below as an example.

SYNTHESIS OF COMPOUND (14)

136 g of pentaerythritol was dissolved in 350 ml of pyridine and 300 ml of acetonitrile and to the solution was added dropwise 562 g of benzoyl chloride under cooling with ice. After the completion of the dropwise addition, the mixture was stirred for 30 minutes at room temperature and the reaction solution was poured into cool diluted hydrochloric acid. The white crystals thus deposited were collected by filtration, washed with water and dried to obtain 550 g of the crude product of Compound (14). A melting point of the refined compound obtained by recrystallization from methanol was 99° to 100° C.

The heat fusible compounds according to the present invention are dissolved individually or as a mixture of two or more thereof in an auxiliary solvent together with photographic additives such as a dye releasing redox compound and then dispersed in an aqueous solution of a hydrophilic colloid using a dispersing aid. Examples of the dispersing methods to be used are described, for example, in U.S. Pat. Nos. 2,304,939, 2,322,027, 2,801,170, 2,801,171 and 2,949,360, etc. Examples of the auxiliary solvents used include a low alkyl acetate such as ethyl acetate, butyl acetate, etc., ethyl propionate, secondary butyl alcohol, methyl isobutyl ketone, β-ethoxyethyl acetate, methyl cellosolve acetate, cyclohexanone, etc.

The heat fusible compounds according to the present invention may be used together with a compound having a high boiling point, for example, a phthalic acid alkyl ester (for example, dibutyl phthalate, dioctyl phthalate, etc.), a phosphoric acid ester (for example, diphenyl phosphate, triphenyl phosphate, tricresyl phosphate, dioctyl butyl phosphate, etc.), a citric acid ester (for example, tributyl acetyl citrate, etc.), a benzoic acid ester (for example, octyl benzoate, etc.), an alkylamine (for example, diethyllaurylamide, etc.), a fatty acid ester (for example, dibutoxyethyl succinate, dioctyl azelate, etc.), etc.

Examples of the dispersing aids usually used include an anionic surface active agent (for example, sodium alkylbenzenesulfonate, sodium dioctylsulfosuccinate, sodium dodecylsulfate, sodium alkylnaphthalenesulfonate, a Fisher type coupler, etc.), an amphoteric surface active agent (for example, N-tetradecyl-N,N-dipolyethylene-α-betaine, etc.), a nonionic surface active agent (for example, sorbitan monolaurate, etc.), etc.

The heat fusible compound according to the present invention can be used in a range from 0.05 to 20 times by weight based on the dye releasing redox compound. Preferably, they can be used in a range from 0.1 to 5 times by weight based on the dye releasing redox compound.

Particularly preferred examples of silver halide used in the present invention partially contain a silver iodide crystal in its particle. That is, the silver halide the X-ray diffraction pattern of which show that of pure silver iodide are particularly preferred.

In the photographic material, a silver halide containing at least two silver halides each having different halogen may be used. Such silver halides yield a completely mixed crystal in a conventional silver halide emulsion. For example, the particle of silver iodobromide shows X-ray diffraction pattern at a position corresponding to the mixed ratio of silver iodide crystal and silver bromide crystal but not at a position corresponding to pure silver iodide crystal and pure silver bromide crystal separately.

Particularly preferred examples of silver halide used in the present invention include silver chloroiodide, silver iodobromide, and silver chloroiodobromide each containing silver iodide crystal in its particle and showing X-ray diffraction pattern at a position corresponding to pure silver iodide crystal.

The process for preparing those silver halides is explained taking the case of silver iodobromide. That is, the silver iodobromide is prepared by adding silver nitride solution to potassium bromide solution to form silver bromide and further adding potassium iodide to the mixing solution.

The silver halide has a particle size of from 0.001 μm to 2 μm and, preferably, from 0.001 μm to 1 μm.

The silver halide used in the present invention may be used as is. However, it may be chemically sensitized with a chemical sensitizing agent such as compounds of sulfur, selenium or tellurium, etc., or compounds of gold, platinum, palladium, rhodium or iridium, etc., a reducing agent such as tin halide, etc., or a combination thereof. The details thereof are described in T. H. James, *The Theory of the Photographic Process*, the Fourth Edition, Chapter 5, pages 149 to 169.

In particularly preferred embodiments according to the present invention, an organic silver salt oxidizing agent is used together with. The organic silver salt oxidizing agent which can be used in the present invention is a silver salt which is comparatively stable to light and which forms a silver image by reacting with the above described image forming compound or a reducing agent coexisting, if necessary, with the image forming compound, when it is heated to a temperature of above 80° C. and, preferably, above 100° C. in the presence of exposed silver halide. By coexisting the organic silver salt oxidizing agent in the photographic material of the present invention, a high density of color image can be obtained.

An amount of the organic silver salt oxidizing agent used is in a range from 0 to 100 mol, and preferably, from 0.2 to 10 mols per mol of the silver halide.

Examples of such organic silver salt oxidizing agent include the following compounds.

A silver salt of an organic compound having a carboxy group. Typical examples thereof include a silver salt of an aliphatic carboxylic acid and a silver salt of an aromatic carboxylic acid.

Examples of the silver salts of aliphatic carboxylic acids include silver behenate, silver stearate, silver oleate, silver laurate, silver caprate, silver myristate, silver palmitate, silver maleate, silver fumarate, silver tartarate, silver furoate, silver linolate, silver oleate, silver adipate, silver sebacate, silver succinate, silver acetate, silver butyrate and silver camphorate, etc. These silver salts which are substituted with a halogen atom or a hydroxyl group are also effectively used.

Examples of the silver salts of aromatic carboxylic acid and other carboxyl group containing compounds include silver benzoate, a silver substituted benzoate such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenylbenzoate, etc., silver gallate, silver tannate, silver phthalate, silver terephthalate, silver salicylate, silver phenylacetate, silver pyromellitate, a silver salt of 3-carboxymethyl-4-methyl-4-thiazoline-2-thione or the like as described in U.S. Pat. No. 3,785,830, and a silver salt of an aliphatic carboxylic acid containing a thioether group as described in U.S. Pat. No. 3,330,663, etc.

In addition, a silver salt of a compound containing a mercapto group or a thione group and a derivative thereof can be used.

Examples of these compounds include a silver salt of 3-mercapto-4-phenyl-1,2,4-triazole, a silver salt of 2-mercaptobenzimidazole, a silver salt of 2-mercapto-5-aminothiadiazole, a silver salt of 2-mercaptobenzothiazole, a silver salt of 2-(S-ethylglycolamido)benzothiazole, a silver salt of thioglycolic acid such as a silver salt of an S-alkyl thioglycolic acid (wherein the alkyl group has from 12 to 22 carbon atoms) as described in Japanese Patent Application (OPI) No. 28221/73, a silver salt of dithiocarboxylic acid such as a silver salt of dithioacetic acid, a silver salt of thioamide, a silver salt of 5-carboxyl-1-methyl-2-phenyl-4-thiopyridine, a silver salt of mercaptotriazine, a silver salt of 2-mercaptobenzoxazole, a silver salt of mercaptooxadiazole, a silver salt as described in U.S. Pat. No. 4,123,274, for example, a silver salt of 1,2,4-mercaptotriazole derivative such as a silver salt of 3-amino-5-benzylthio-1,2,4-triazole, a silver salt of thione compounds such as a silver salt of 3-(2-carboxyethyl)-4-methyl-4-thiazoline-2-thione as described in U.S. Pat. No. 3,301,678, and the like.

Further, a silver salt of a compound containing an imino group can be used. Examples of these compounds include a silver salt of benzotriazole and a derivative thereof as described in Japanese Patent Publication Nos. 30270/69 and 18416/70, for example, a silver salt of benzotriazole, a silver salt of alkyl substituted benzotriazole such as a silver salt of methylbenzotriazole, etc., a silver salt of a halogen substituted benzotriazole such as a silver salt of 5-chlorobenzotriazole, etc., a silver salt of carboimidobenzotriazole such as a silver salt of butyl-carboimidobenzotriazole, etc., a silver salt of 1,2,4-triazole or 1-H-tetrazole as described in U.S. Pat. No. 4,220,709, a silver salt of carbazole, a silver salt of saccharin, a silver salt of imidazole and an imidazole derivative, and the like.

Moreover, a silver salt as described in *Research Disclosure*, Vol. 170, No. 17029 (June, 1978) and an organic metal such as copper stearate, etc., are examples of the organic metal salt oxidizing agent capable of being used in the present invention.

The mechanism of the heat-development process under heating in the present invention is not entirely clear, but it is believed to be as follows.

When the photographic material is exposed to light, a latent image is formed in a light-sensitive silver halide. This phenomenon is described in T. H. James, *The Theory of the Photographic Process*, Third Edition, pages 105 to 148.

When the photographic material is heated, the reducing agent, the dye releasing redox compound, in the case of the present invention reduces the silver halide or the silver halide and the organic silver salt oxidizing agent in the presence of the latent image nuclei as a catalyst to form silver, while it is oxidized itself. The oxidized product of the dye releasing redox compound is attached by a nucleophilic reagent (a dye releasing activator in the case of the present invention) to release a dye.

When the organic silver salt oxidizing agent is co-employed in the photographic material of the present invention, the silver halide and the organic silver salt oxidizing agent which form a starting point of development should be present within a substantially effective distance.

For this purpose, it is desired that the silver halide and the organic silver salt oxidizing agent are present in the same layer or two layers adjacent to each other.

The silver halide and the organic metal salt oxidizing agent which are separately formed can be mixed prior to use to prepare a coating solution, but it is also effective to blend both of them in a ball mill for a long period of time. Further, it is effective to use a process which comprises adding a halogen containing compound to the organic silver salt oxidizing agent prepared to form silver halide using silver of the organic silver salt oxidizing agent.

Method of preparing these silver halide and organic silver salt oxidizing agents and manners of blending them are described in *Research Disclosure*, No. 17029, Japanese Patent Application (OPI) Nos. 32928/75 and 42529/76, U.S. Pat. No. 3,700,458, and Japanese Patent Application (OPI) Nos. 13224/74 and 17216/75.

A suitable coating amount of the light-sensitive silver halide and the organic silver salt oxidizing agent employed in the present invention is in a total of from 50 mg to 10 g/m² calculated as an amount of silver.

The light-sensitive silver halide and the organic silver salt oxidizing agent used in the present invention are prepared in the binder as described below. Further, the dye releasing redox compound is dispersed in the binder described below.

The binder which can be used in the present invention can be employed individually or in a combination of two or more. The typical hydrophilic binder is a transparent or translucent hydrophilic colloid, examples of which include a natural substance, for example, protein such as gelatin, a gelatin derivative, a cellulose derivative, a polysaccharide such as starch, gum arabic, etc., and a synthetic polymer, for example, a water-soluble polyvinyl compound such as polyvinyl pyrrolidone, acrylamide polymer, etc. Another example of the synthetic polymer compound is a dispersed vinyl compound in a latex form which is used for the purpose of increasing dimensional stability of a photographic material.

The dye releasing redox compound which releases a hydrophilic diffusible dye used in the present invention is represented by the following general formula (X):

$$R-SO_2-D \qquad (X)$$

where R represents a reducing group capable of being oxidized by the silver halide; and D represents an image forming dye portion containing a hydrophilic group.

Preferably, the reducing group represented by R in the dye releasing redox compound $R-SO_2-D$ has an oxidation-reduction potential to a saturated calomel electrode of 1.2 V or less measuring the polarographic half wave potential using acetonitrile as a solvent and sodium perchlorate as a base electrolyte. Preferred examples of the reducing group R include those represented by the following general formulae (XI) to (XIX).

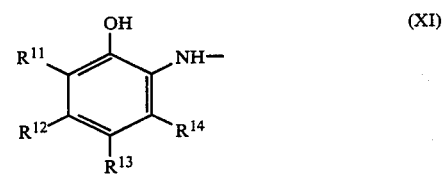

(XI)

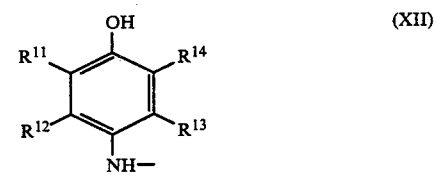

(XII)

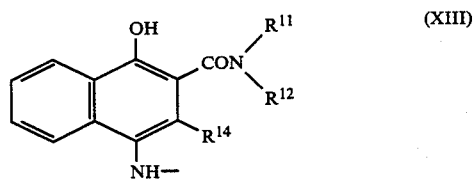

(XIII)

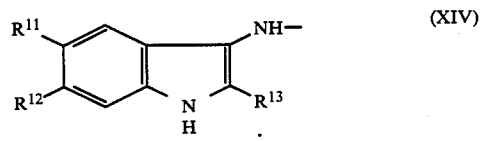

(XIV)

-continued

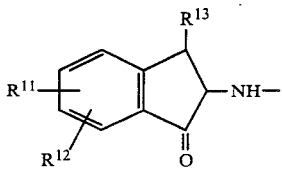
(XV)

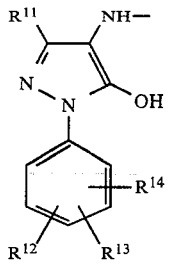

(XVI)

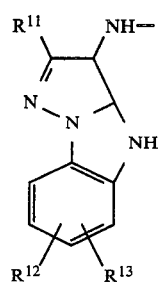
(XVII)

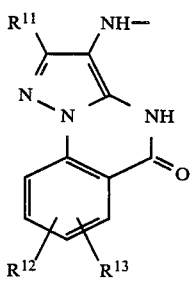
(XIX)

wherein $R^{11}$, $R^{12}$, $R^{13}$ and $R^{14}$ each represents a hydrogen atom or a substituent selected from an alkyl group, a cycloalkyl group, an aryl group, an alkoxy group, an aryloxy group, an aralkyl group, an acyl group, an acylamino group, an alkylsulfonyamino group, an arylsulfonylamino group, an aryloxyalkyl group, an alkoxyalkyl group, an N-substituted carbamoyl group, an N-substituted sulfamoyl group, a halogen atom, an alkylthio group or an arylthio group. The alkyl moiety and the aryl moiety in the above described substituents may be further substituted with an alkoxy group, a halogen atom, a hydroxy group, a cyano group, an acyl group, an acylamino group, a substituted carbamoyl group, a substituted sulfamoyl group, an alkylsulfonylamino group, an arylsulfonylamino group, a substituted ureido group or a carbalkoxy group. Furthermore, the hydroxy group and the amino group included in the reducing group represented by R may be protected by a protective group capable of reproducing the hydroxy group and the amino group by the action of a nucleophilic agent.

In more preferred embodiments of the present invention, the reducing group R is represented by the following general formula (XX).

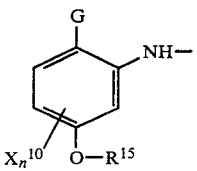
(XX)

wherein G represents a hydroxy group or a group giving a hydroxy group upon hydrolysis; $R^{15}$ represents an alkyl group or an aromatic group; $X^{10}$ represents an electron donating substituent when n is 1 or substituents, which may be the same or different, one of the substituents being an electron donating group and the second or second and third substituents being selected from the group consisting of an electron donating group or a halogen atom when n is 2 or 3; wherein $X^{10}$ groups may form a condensed ring with each other or with $OR^{15}$; n is 1, 2 or 3 and the total carbon number of $X_n^{10}$ and $R^{15}$ is not less than 8.

Of the reducing groups represented by the general formula (XX), more preferred reducing groups R are represented by the following general formulae (XXa) and (XXb):

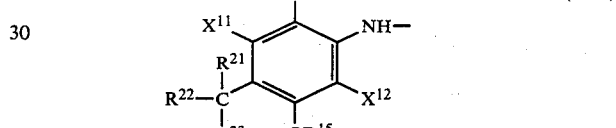
(XXa)

wherein G represents a hydroxy group or a group having a hydroxy group upon hydrolysis; $R^{21}$ and $R^{22}$, which may be the same or different, each represents an alkyl group or $R^{21}$ and $R^{22}$ may be bonded to each other to form a ring; $R^{23}$ represents a hydrogen atom or an alkyl group; $R^{15}$ represents an alkyl group or an aromatic group; $X^{11}$ and $X^{12}$, which may be the same or different, each represents a hydrogen atom, an alkyl group, an alkoxy group, a halogen atom, an acylamino group or an alkylthio group; and $R^{15}$ and $X^{12}$ or $R^{15}$ and $R^{23}$ may be bonded to each other to form a ring,

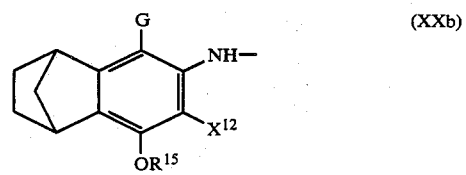
(XXb)

wherein G represents a hydroxy group or a group giving a hydroxy group upon hydrolysis; $R^{15}$ represents an alkyl group or an aromatic group; $X^{12}$ represents a hydrogen atom, an alkyl group, an alkoxy group, a halogen atom, an acylamino group or an alkylthio group; and $R^{15}$ and $X^{12}$ may be bonded to each other to form a ring.

Specific examples of the reducing groups represented by the above described general formulae (XX), (XXa) and (XXb) are described in U.S. Pat. No. 4,055,428, Japanese Patent Application (OPI) Nos. 12642/81 and 16130/81.

In other more preferred embodiments of the present invention, the reducing group R is represented by the following general formula (XXI).

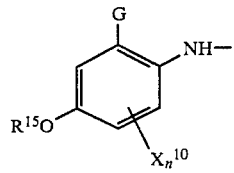
(XXI)

wherein G, $R^{15}$, $X^{10}$ and n each has the same meaning as defined in the general formula (XX).

Of the reducing groups represented by the general formula (XXI), more preferred reducing groups R are represented by the following general formulae (XXIa), (XXIb) and (XXIc).

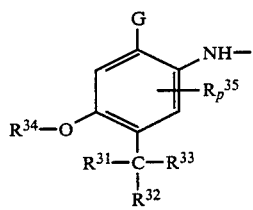
(XXIa)

wherein G represents a hydroxy group or a group giving a hydroxy group upon hydrolysis; $R^{31}$ and $R^{32}$, which may be the same or different, each represents an alkyl group or an aromatic group, and $R^{31}$ and $R^{32}$ may be bonded to each other to form a ring; $R^{33}$, represents a hydrogen atom, an alkyl group or an aromatic group; $R^{34}$ represents an alkyl group or an aromatic group; $R^{35}$ represents an alkyl group, an alkoxy group, an alkylthio group, an arylthio group, a halogen atom or an acylamino group; p is 0, 1 or 2; $R^{34}$ and $R^{35}$ may be bonded to each other to form a condensed ring; $R^{31}$ and $R^{34}$ may be bonded to each other to form a condensed ring; $R^{31}$ and $R^{35}$ may be bonded to each other to form a condensed ring; and the total number of the carbon atoms included in $R^{31}$, $R^{32}$, $R^{33}$, $R^{34}$ and $R^{35}$ p is more than 7.

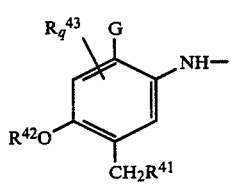
(XXIb)

wherein G represents a hydroxy group or a group giving a hydroxy group upon hydrolysis; $R^{41}$ represents an alkyl group or an aromatic group; $R^{42}$ represents an alkyl group or an aromatic group; $R^{43}$ represents an alkyl group, an alkoxy group, an alkylthio group, an arylthio group, a halogen atom or an acylamino group; q is 0, 1 or 2; $R^{42}$ and $R^{43}$ may be bonded to each other to form a condensed ring; $R^{41}$ and $R^{42}$ may be bonded to each other to form a condensed ring; $R^{41}$ and $R^{43}$ may be bonded to each other to form a condensed ring; and the total number of the carbon atoms included in $R^{41}$, $R^{42}$ and $R^{43}$ q is more than 7.

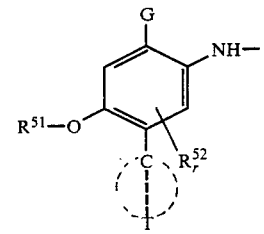
(XXIc)

wherein G represents a hydroxy group or a group giving a hydroxy group upon hydrolysis; $R^{51}$ represents an alkyl group or an aromatic group; $R^{52}$ represents an alkyl group, an alkoxy group, an alkylthio group, an arylthio group, a halogen atom or an acylamino group; r is 0, 1 or 2; the group of

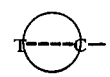

represents a group in which 2 to 4 saturated hydrocarbon rings are condensed, the carbon atom

in the condensed ring which is connected to the phenol nucleus (or a precursor thereof), a tertiary carbon atom which composes one pivot of the condensed ring, a part of the carbon atoms (excluding the above described tertiary carbon atom) in the hydrocarbon ring may be substituted for oxygen atom(s), the hydrocarbon ring may have a substituent, and an aromatic ring may be further condensed to the hydrocarbon ring; $R^{51}$ or $R^{52}$ and the group

may be bonded to each other to form a condensed ring; and the total number of the carbon atoms included in $R^{51}$, $R^{52}$ and the group of

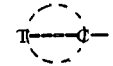

is not less than 7.

Specific examples of the reducing groups represented by the above described general formulae (XXI), (XXIa), (XXIb) and (XXIc) are described in Japanese Patent Application (OPI) Nos. 16131/81, 650/82 and 4043/82.

The essential part in the groups represented by the general formulae (XII) and (XIII) is a para(sulfonyl)aminophenol part. Specific examples of these reducing groups are described in U.S. Pat. No. 3,928,312 and 4,076,529, U.S. Published Patent Application B351,673, U.S. Pat. Nos. 4,135,929 and 4,258,120. These groups are also effective for the reducing group R according to the present invention.

In still other more preferred embodiments of the present invention, the reducing group R is represented by the following general formula (XXII).

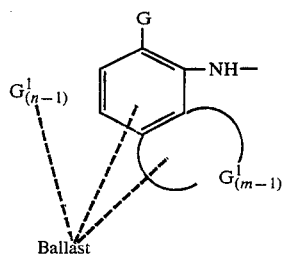

(XXII)

wherein Ballast represents a diffusion resistant group; G represents a hydroxy group or a group giving a hydroxy group upn hydrolysis; $G^1$ represents an aromatic ring directly condensed to the benzene nucleus to form a naphthalene nucleus; and n and m are dissimilar positive integers of 1 to 2.

Specific examples of the reducing groups represented by the above described general formula (XXII) are described in U.S. Pat. No. 4,053,312.

The reducing groups represented by the above described general formulae (XIV), (XVI), (XVII) and (XIX) are characterized by containing a heterocyclic ring. Specific examples of the groups are described in U.S. Pat. No. 4,198,235, Japanese Patent Application (OPI) No. 46730/78, U.S. Pat. No. 4,273,855.

Specific examples of the reducing groups represented by the general formula (XV) are described in U.S. Pat. No. 4,149,892.

Characteristics required for the reducing group R are as follows.

1. It is rapidly oxidized by the silver halide to effectively release a diffusible dye for image formation by the function of the dye releasing activator.
2. The reducing group R has an extensive hydrophobic property, because it is necessary for the dye releasing redox compound to be immobilized in a hydrophilic or hydrophobic binder and that only the released dye have diffusibility.
3. It has excellent stability to heat and to the dye releasing activator and does not release the image forming dye until it is oxidized; and
4. It is easily synthesized.

In the following, specific examples of preferred reducing groups R which satisfy the above described requirements are shown. In the example, NH— represents the bond to the dye portion.

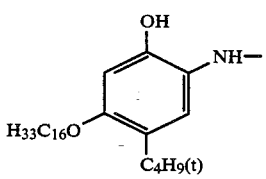

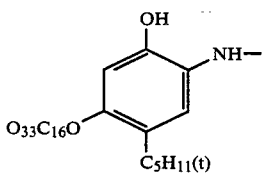

-continued

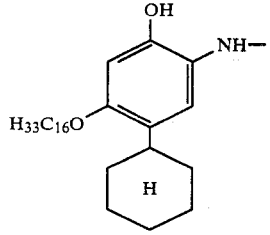

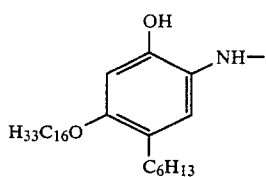

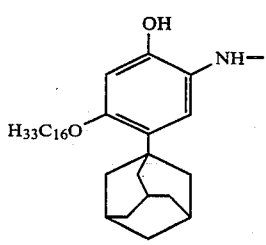

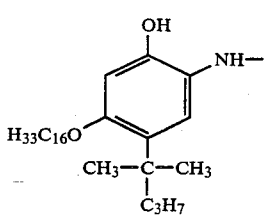

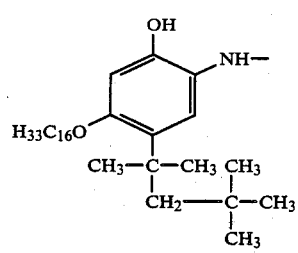

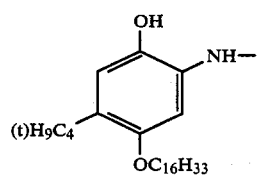

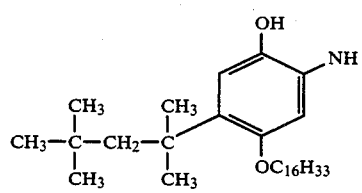

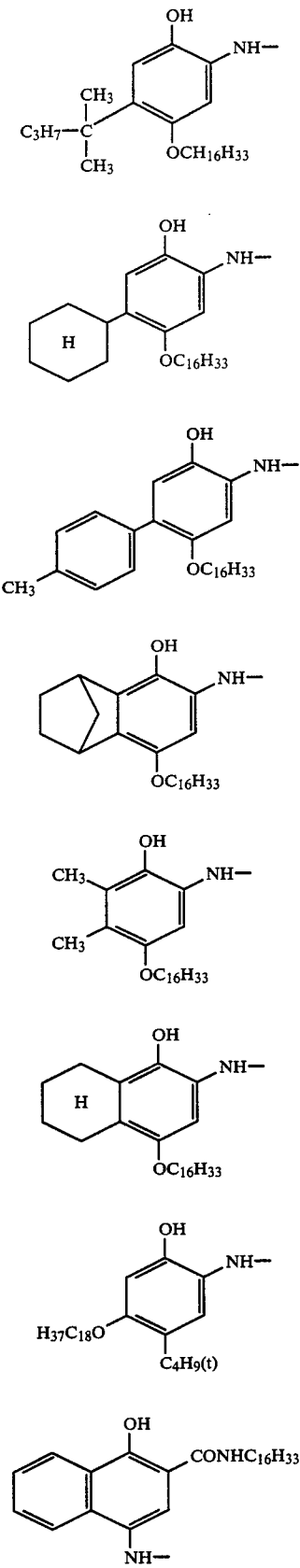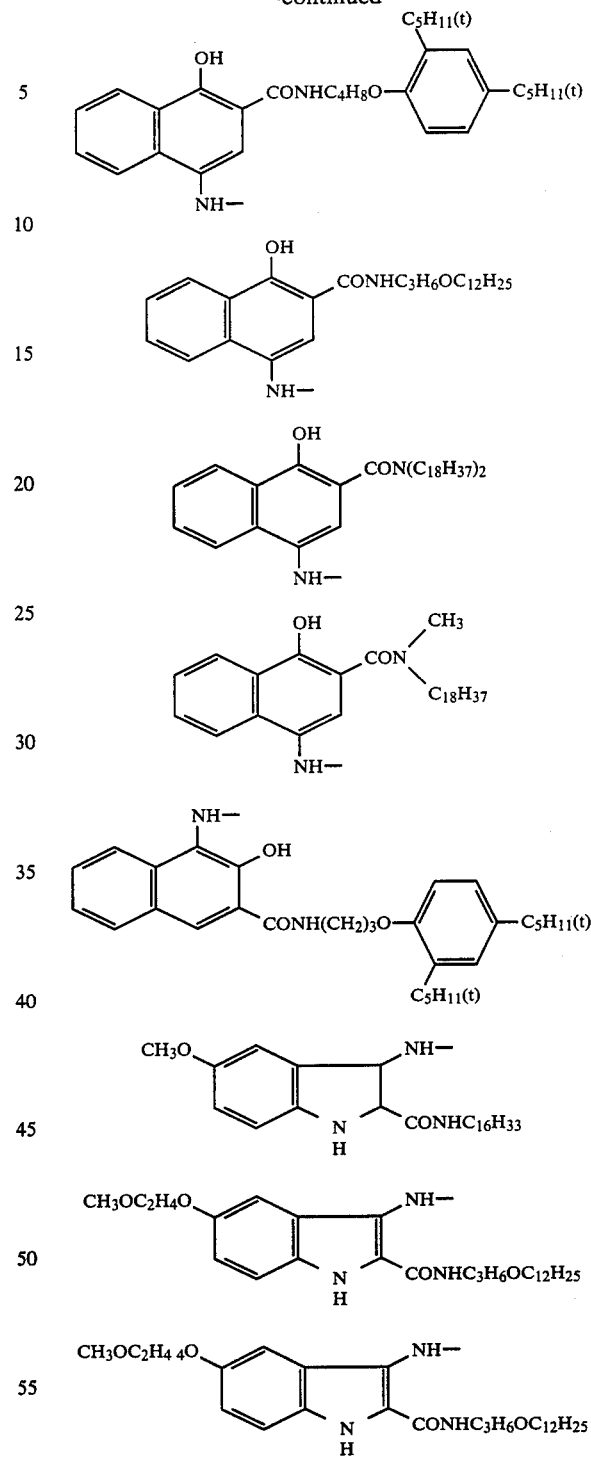

Examples of dyes which can be used for image forming dyes include azo dyes, azomethine dyes, anthraquinone dyes, naphthoquinone dyes, styryl dyes, nitro dyes, quinoline dyes, carbonyl dyes and phthalocyanine dyes, etc. Representative examples of them are set forth below and are classified by hue. Further, these dyes can be used in a temporarily short wavelength shifted form which is capable of regeneration during the development processing.

Yellow:
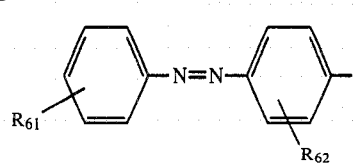
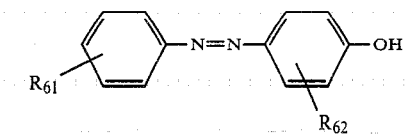
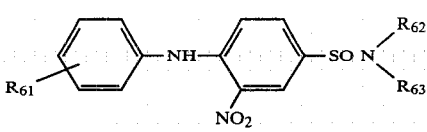
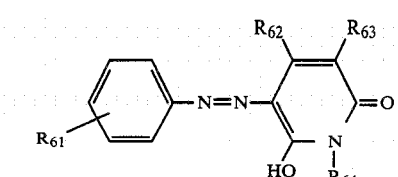
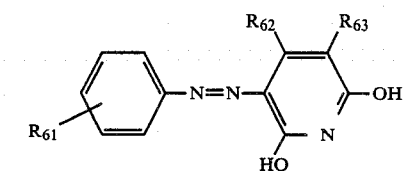
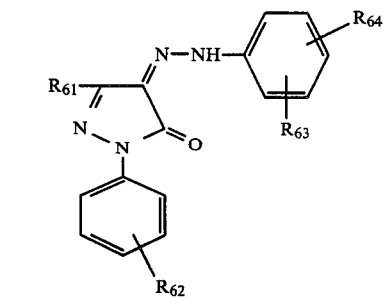
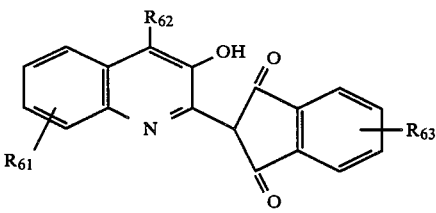
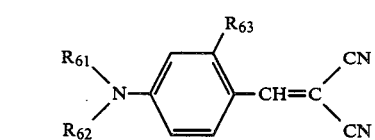
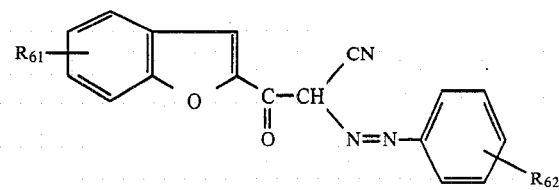
Magenta:
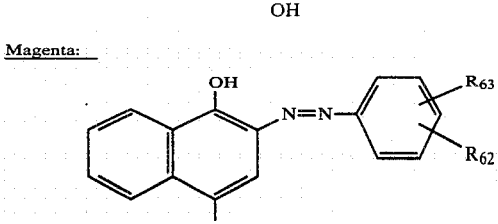
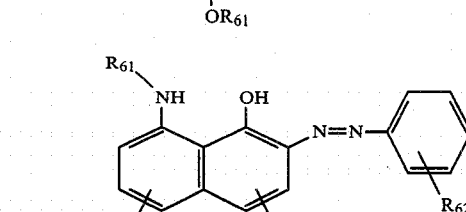
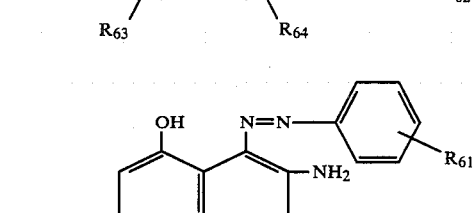
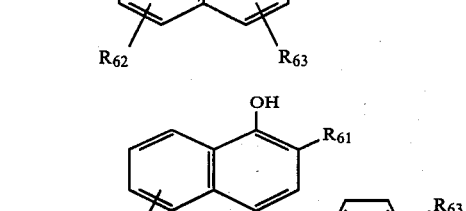
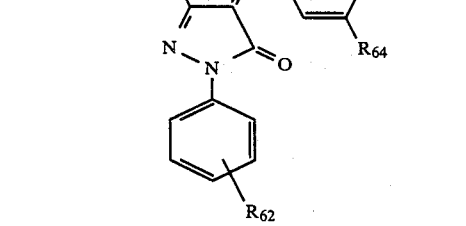

-continued
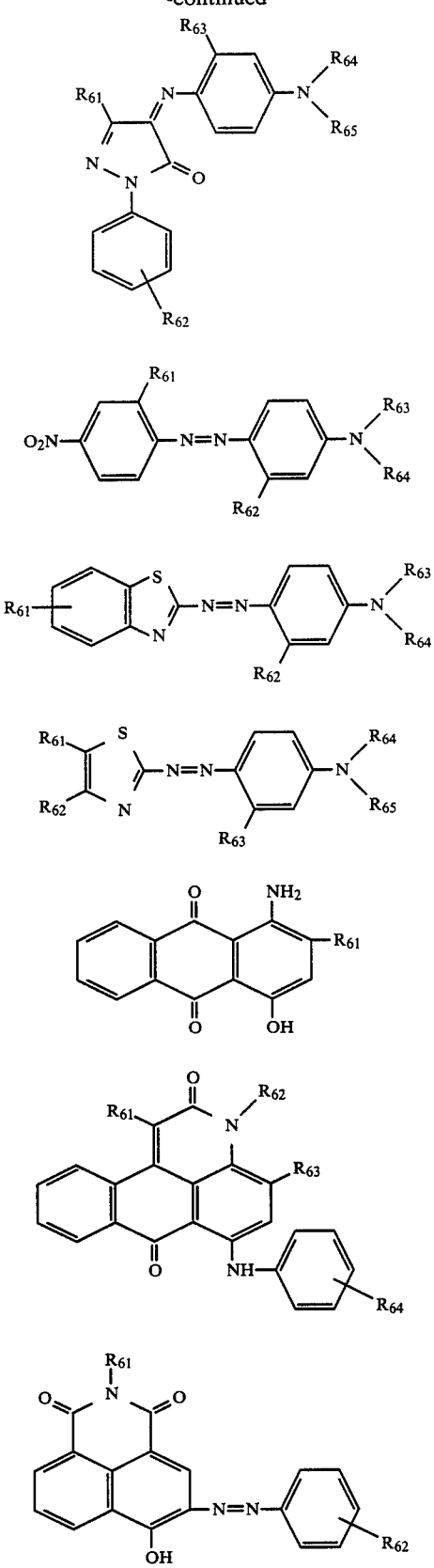
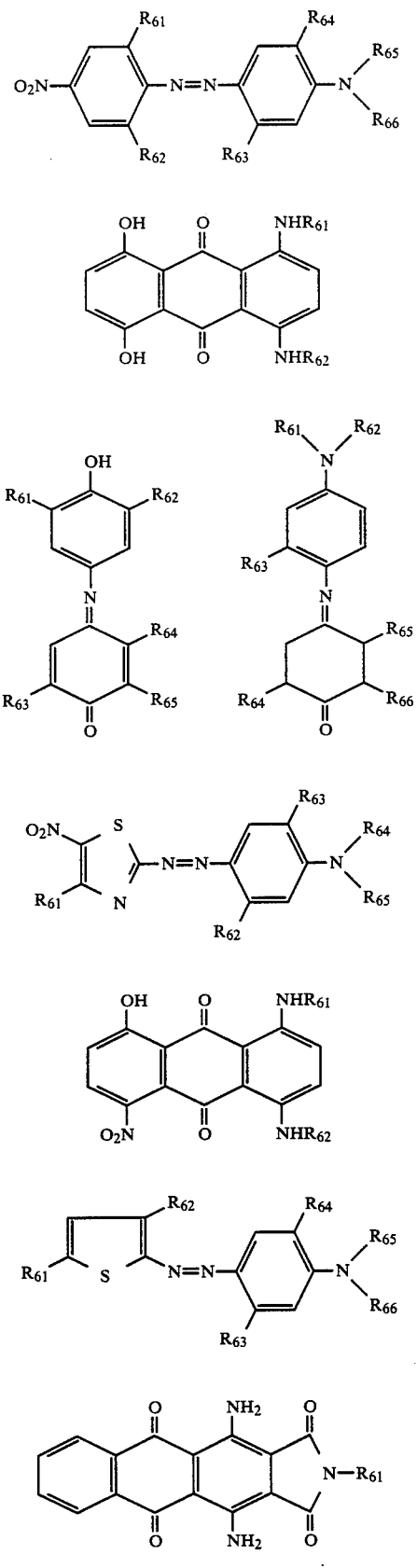
Cyan:

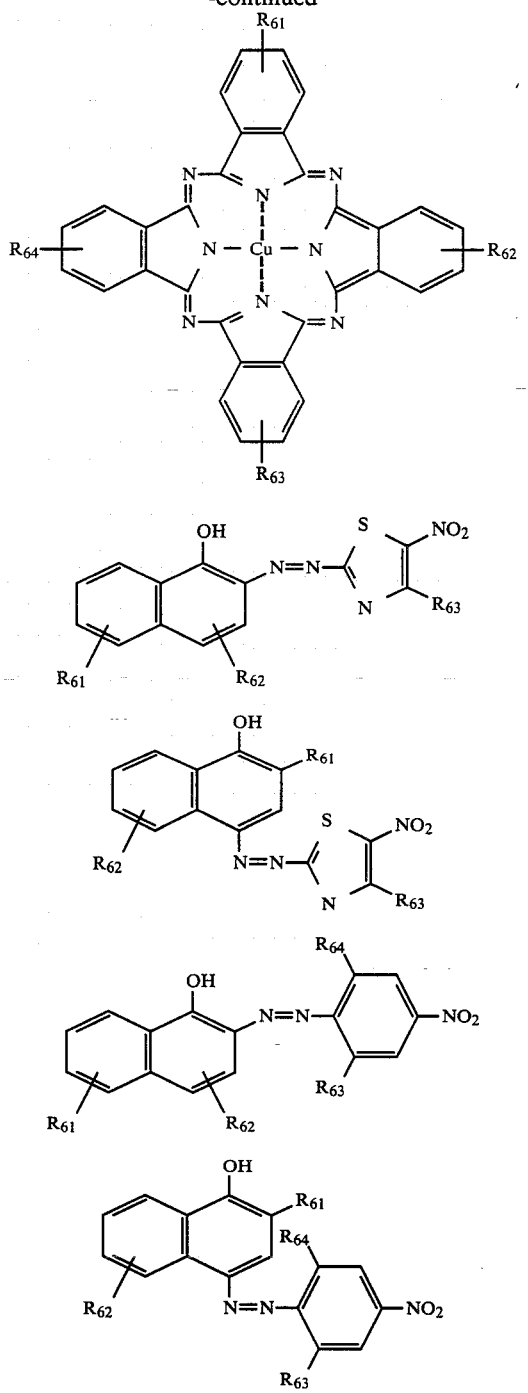

wherein $R^{61}$ to $R^{66}$ each represents a hydrogen atom or a substituent selected from an alkyl group, a cycloalkyl group, an aralkyl group, an alkoxy group, an aryloxy group, an aryl group, an acylamino group, an acyl group, a cyano group, a hydroxyl group, an alkylsulfonylamino group, an arylsulfonylamino group, an alkylsulfonyl group, a hydroxyalkyl group, a cyanoalkyl group, an alkoxycarbonylalkyl group, an alkoxyalkyl group, an aryloxyalkyl group, a nitro group, a halogen atom, a sulfamoyl group, an N-substituted sulfamoyl group, a carbamoyl group, an N-substituted carbamoyl group, an acyloxyalkyl group, an amino group, a substituted amino group, an alkylthio group and an arylthio group. The alkyl moiety and the aryl moiety in the above described substituents may be further substituted with a halogen atom, a hydroxy group, a cyano group, an acyl group, an acylamino group, an alkoxy group, a carbamoyl group, a substituted carbamoyl group, a sulfamoyl group, a substituted sulfamoyl group, a carboxy group, an alkylsulfonylamino group, an arylsulfonylamino group or a ureido group.

Examples of the hydrophilic groups include a hydroxy group, a carboxy group, a sulfo group, a phosphoric acid group, an imido group, a hydroxamic acid group, a quaternary ammonium group, a carbamoyl group, a substituted carbamoyl group, a sulfamoyl group, a substituted sulfamoyl group, a sulfamoylamino group, a substituted sulfamoylamino group, a ureido group, a substituted ureido group, an alkoxy group, a hydroxyalkoxy group, an alkoxyalkoxy group, etc.

In the present invention, those in which the hydrophilic property thereof is increased by dissociation of a proton under a basic condition (pKa<12) are particularly preferred. Examples of these groups include a phenolic hydroxy group, a carboxy group, a sulfo group, a phosphoric acid group, an imido group, a hydroxamic acid group, a (substituted) sulfamoyl group, a (substituted) sulfamoylamino group, etc.

Characteristics required for the image forming dye are as follows.

1. It has a hue suitable for color reproduction.
2. It has a large molecular extinction coefficient.
3. It is fast to light and heat and stable for the dye releasing activator and other additive included in the system; and
4. It is easily synthesized.

Specific examples of preferred image forming dyes which satisfy the above described requirements are described in the following.

Yellow:

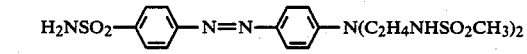

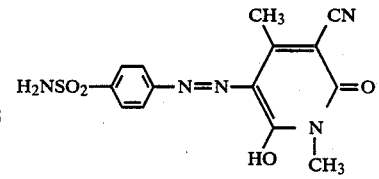

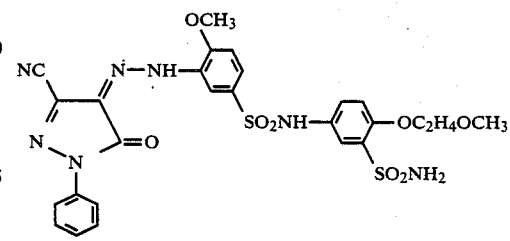

-continued
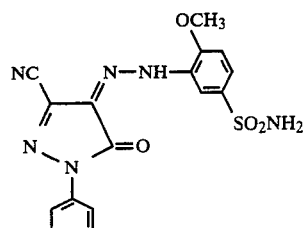
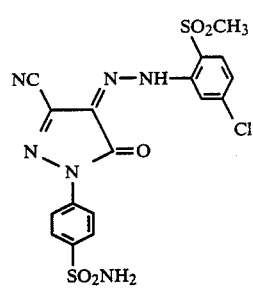
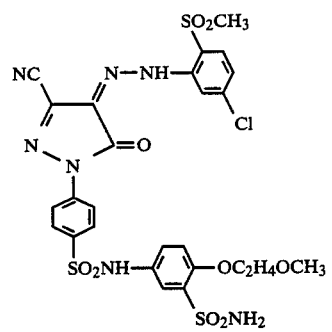
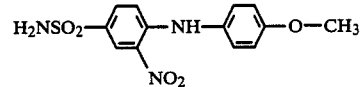
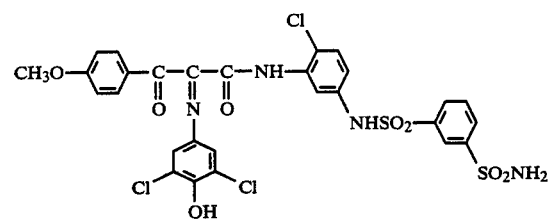
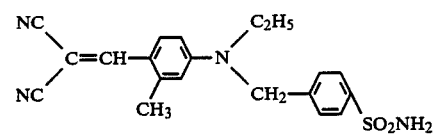
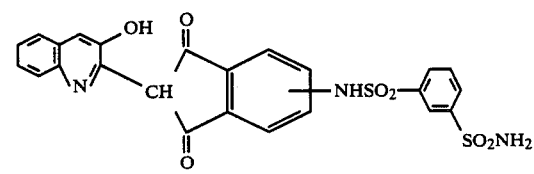
Magenta:
-continued
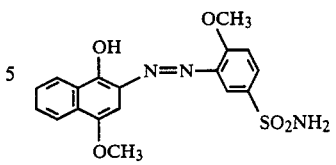
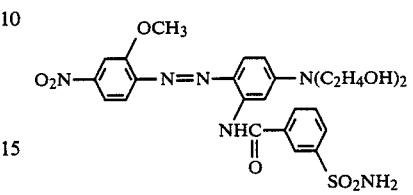
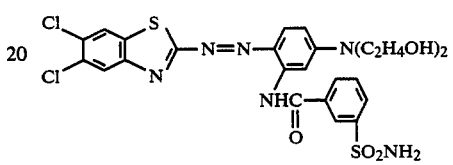
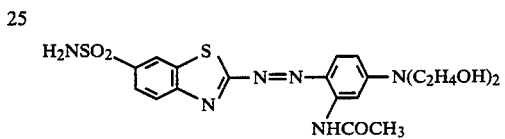
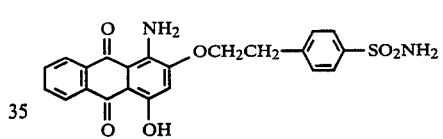
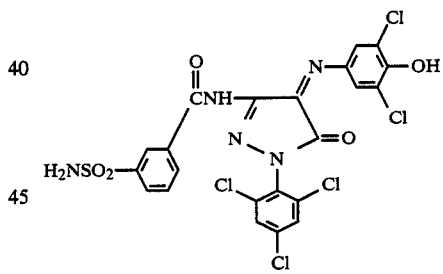
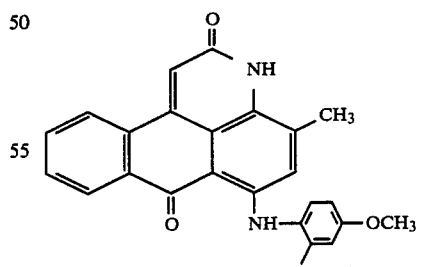
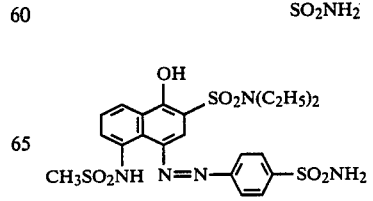

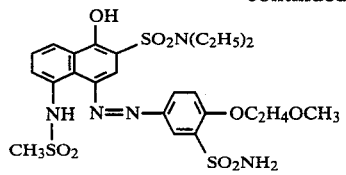
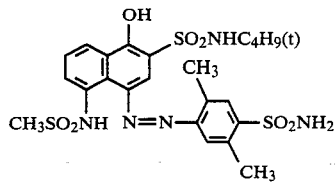
Cyan:
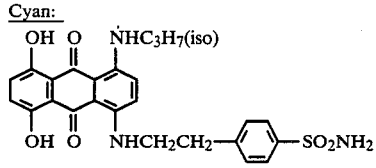
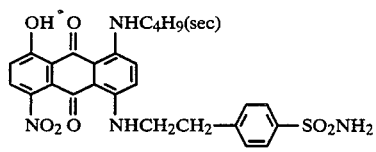
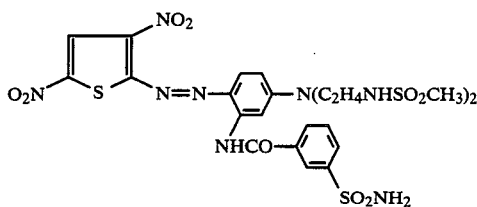
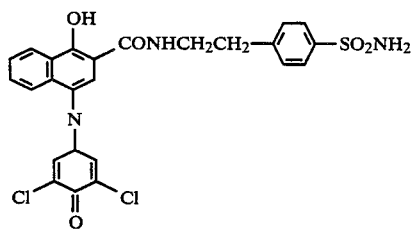
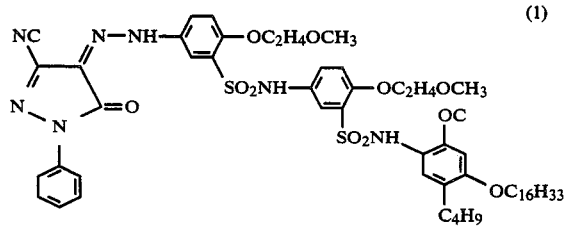
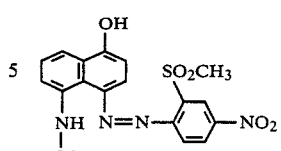
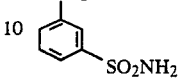
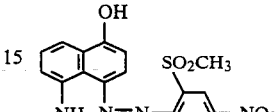
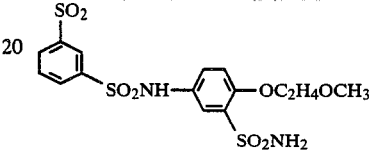
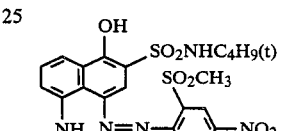
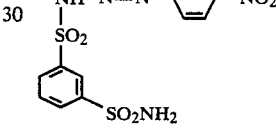
wherein the end group —SO$_2$NH$_2$ in these dyes represents a group necessary to bond to the reducing group R.
In the following, specific examples of the preferred dye releasing redox compounds are described.
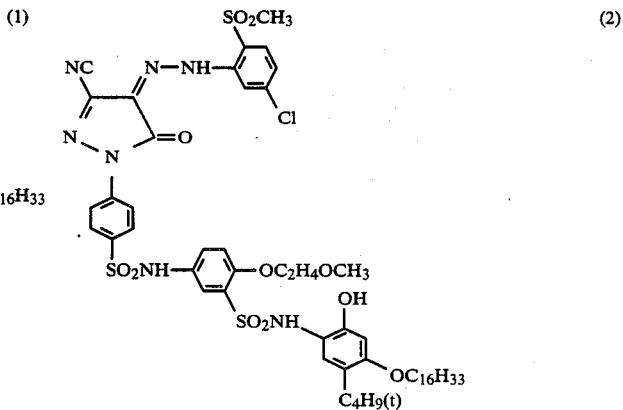

-continued
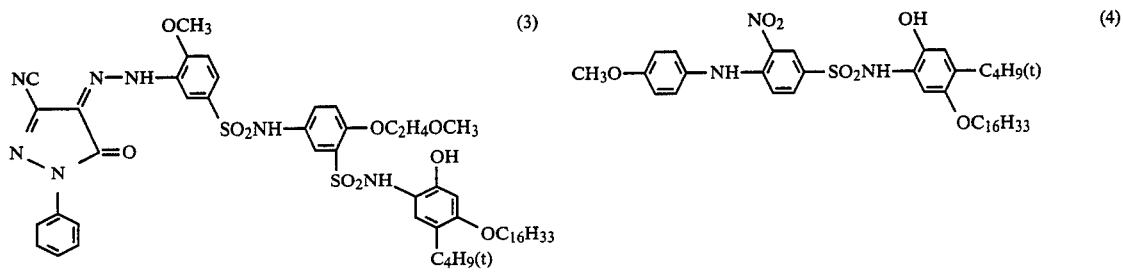
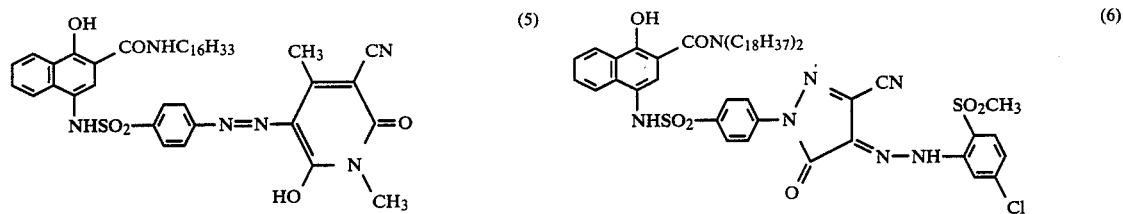
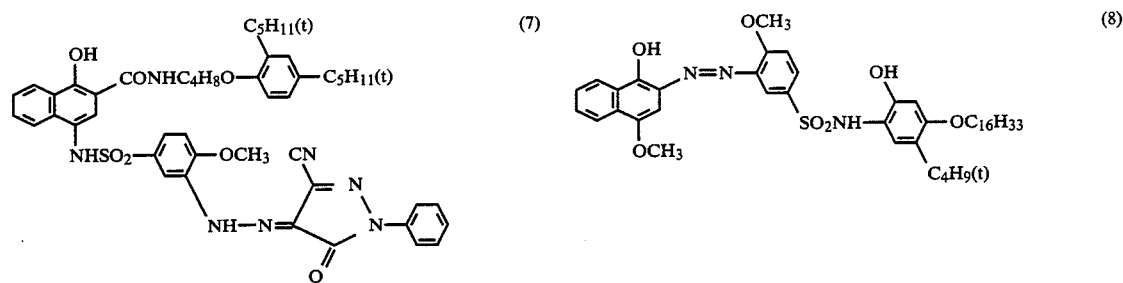
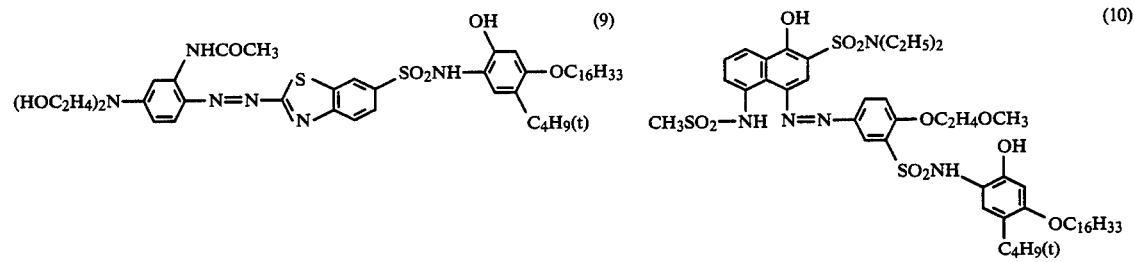
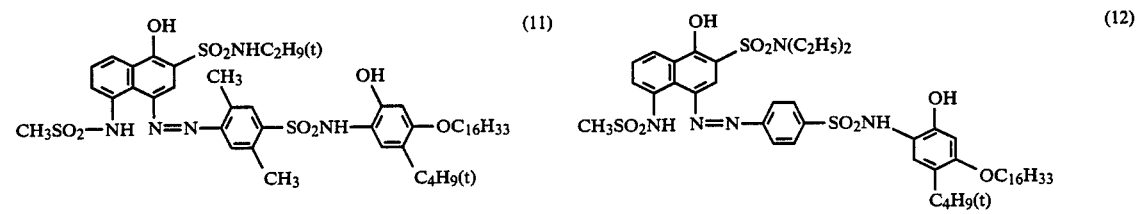

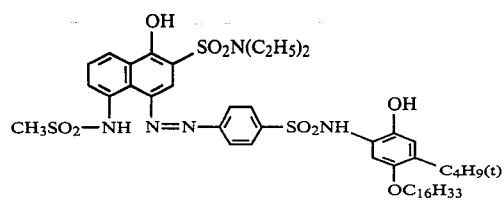 (13)
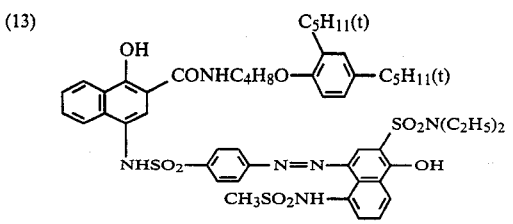 (14)
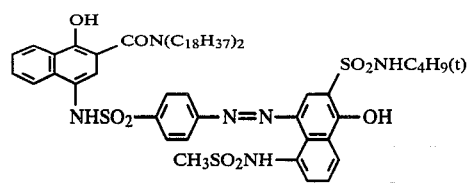 (15)
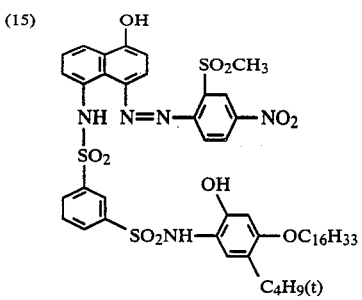 (16)
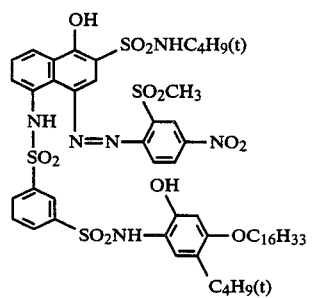 (17)
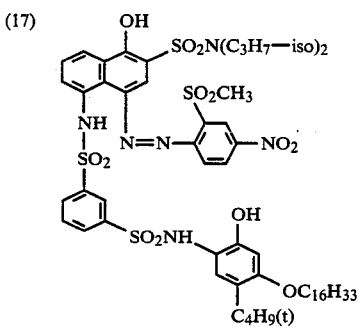 (18)
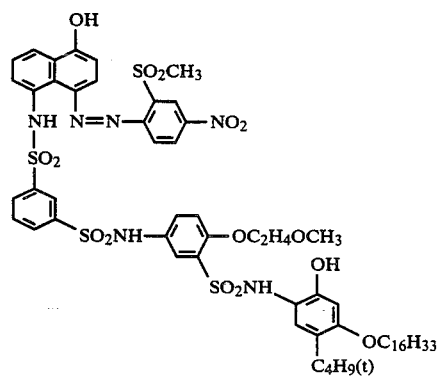 (19)
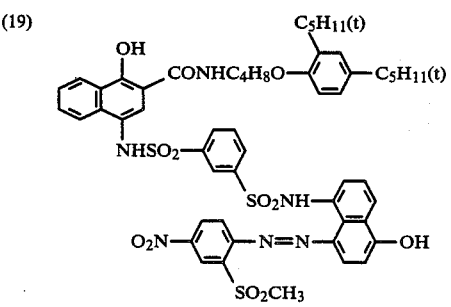 (20)

-continued
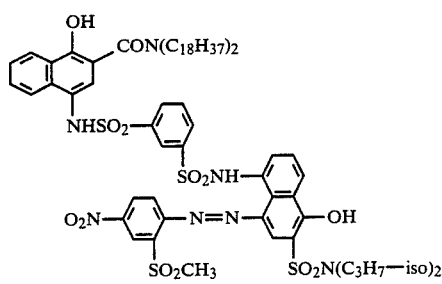 (21)
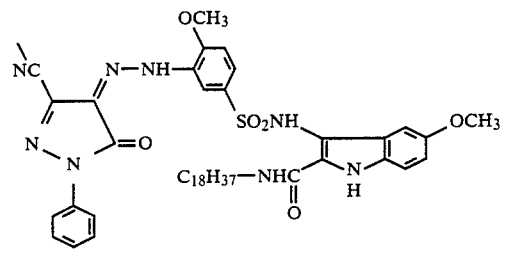 (22)
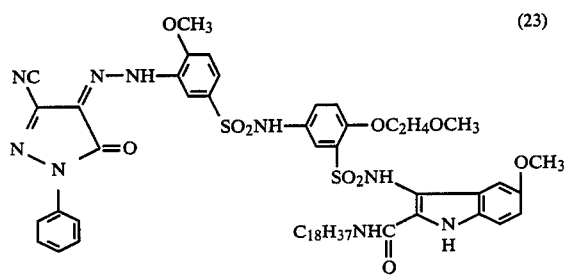 (23)
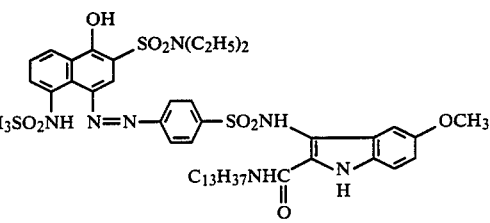 (24)
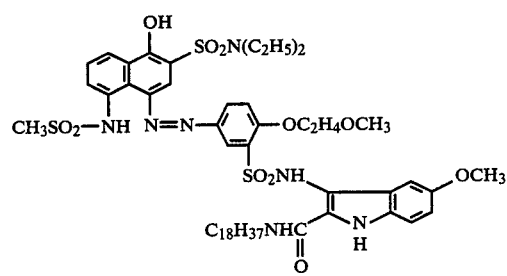 (25)
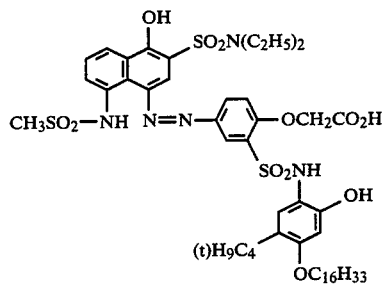 (26)
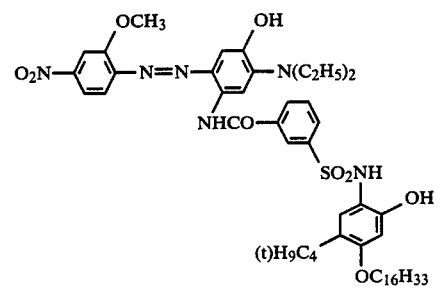 (27)
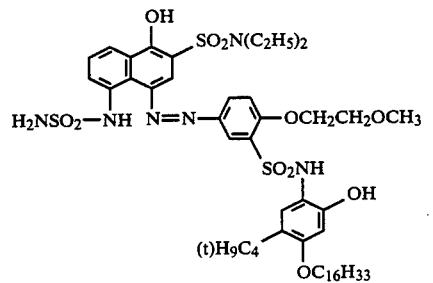 (28)

-continued
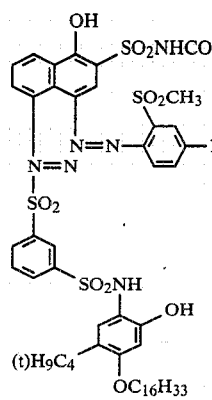 (29)
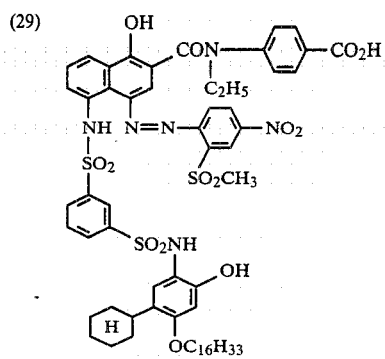 (30)
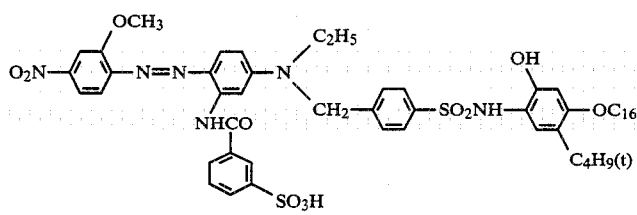 (31)
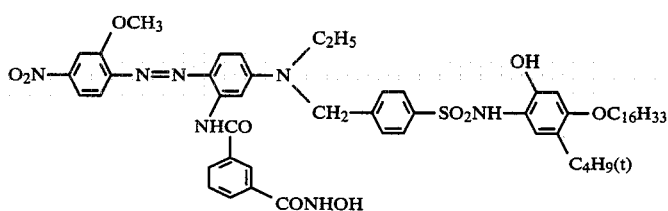 (32)
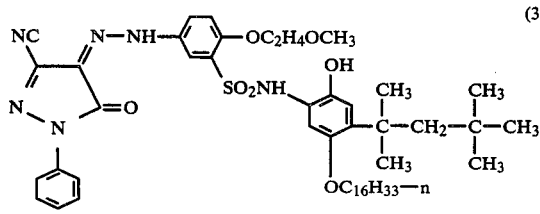 (33)
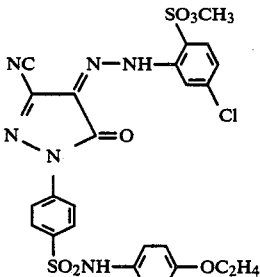 (34)
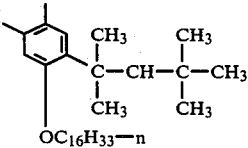

-continued
(35)
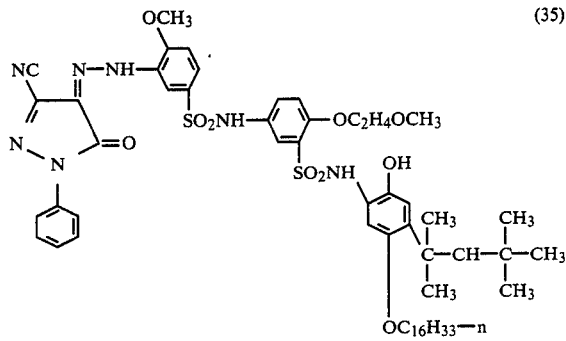
(36)
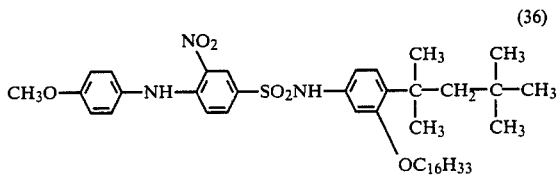
(37)
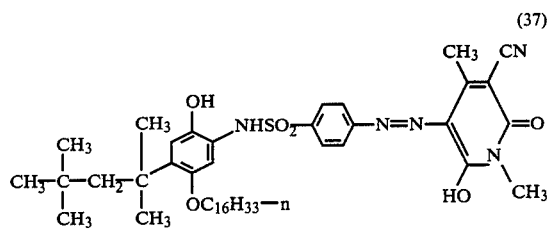
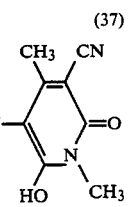
(38)
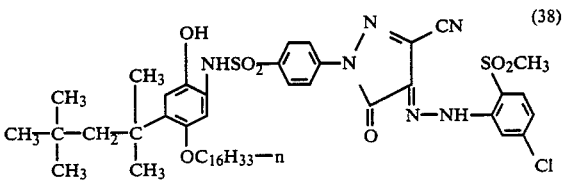
(39)
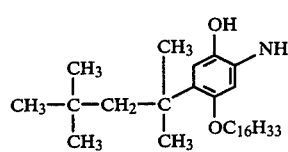
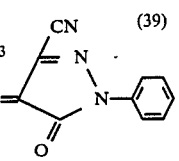
(40)
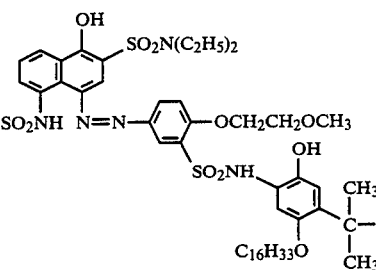
(41)
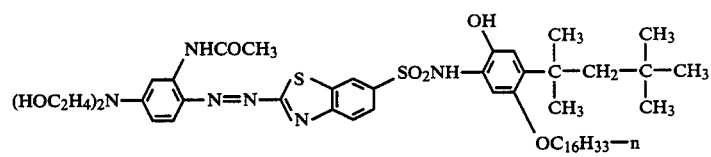
(42)
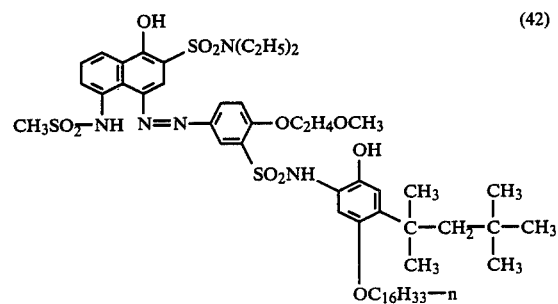
(43)
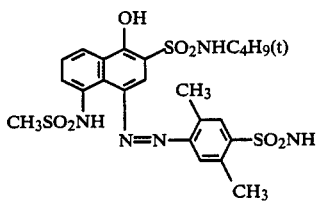

-continued
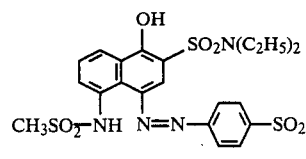 (44)
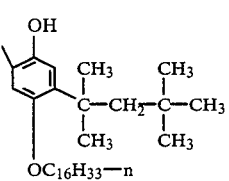
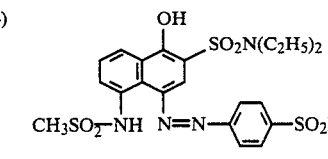 (45)
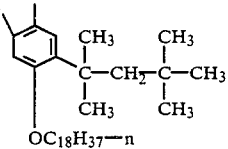
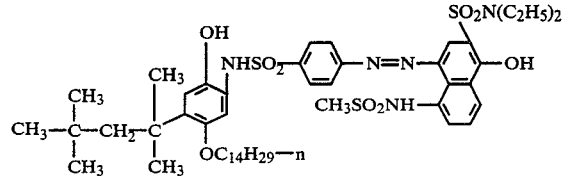 (46)
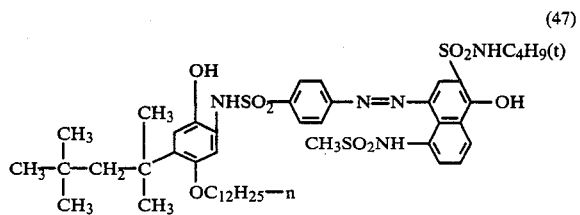 (47)
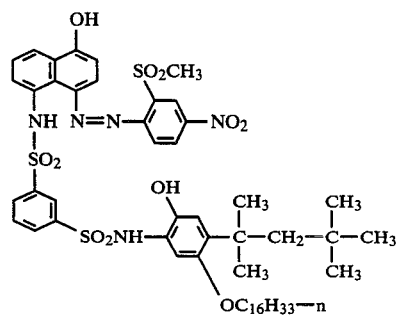 (48)
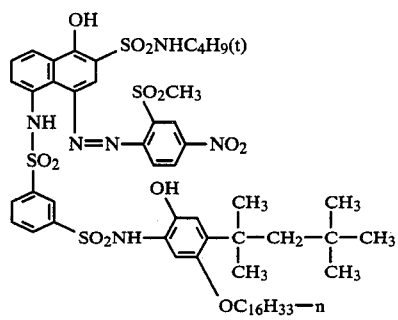 (49)
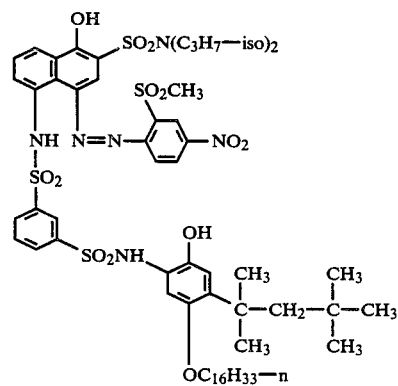 (50)
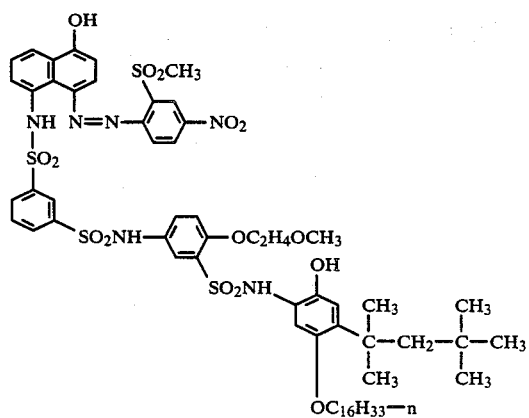 (51)

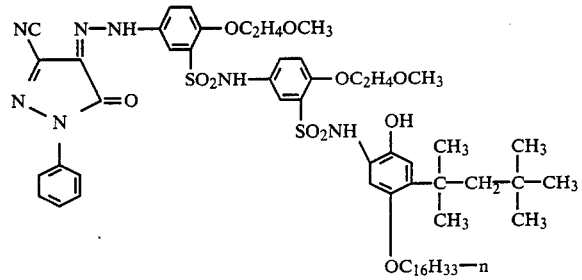 (52)
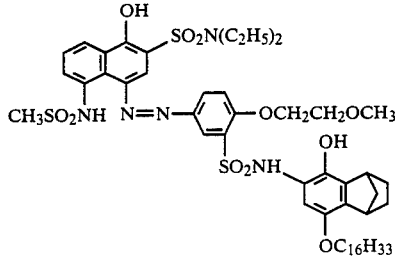 (53)
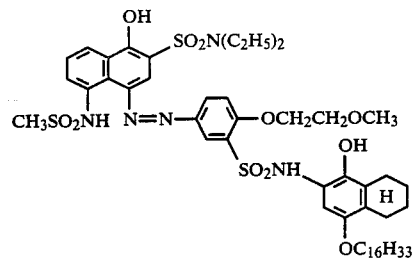 (54)
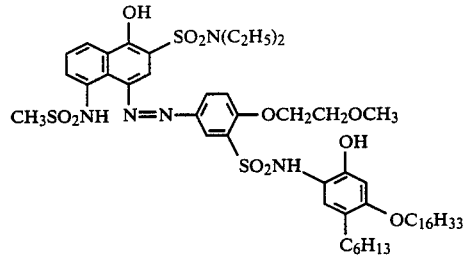 (55)
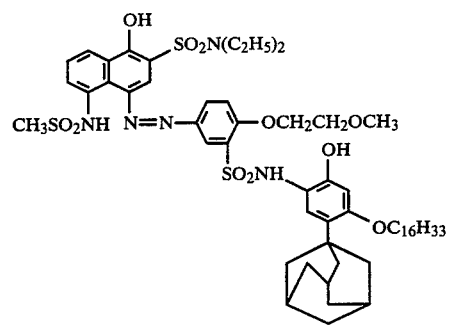 (56)
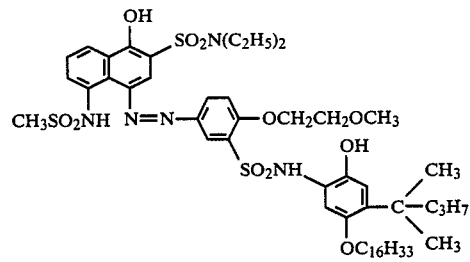 (57)
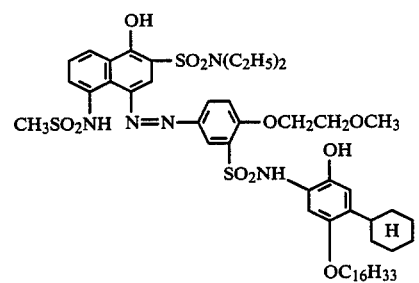 (58)
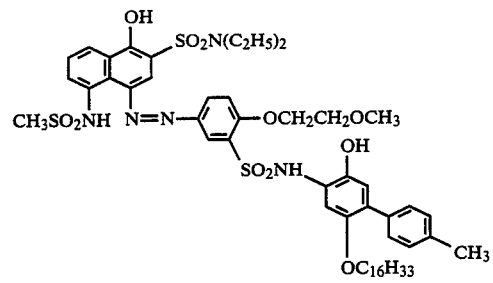 (59)
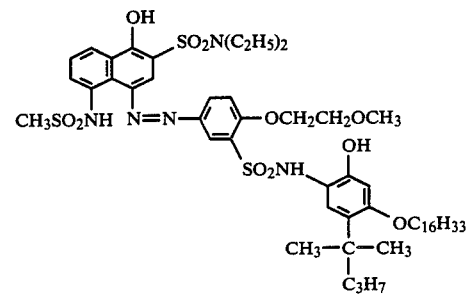 (60)
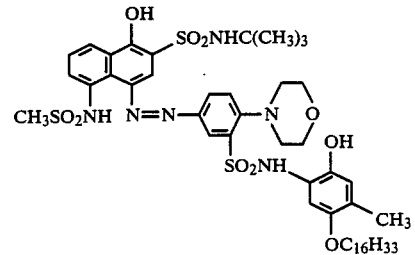 (61)

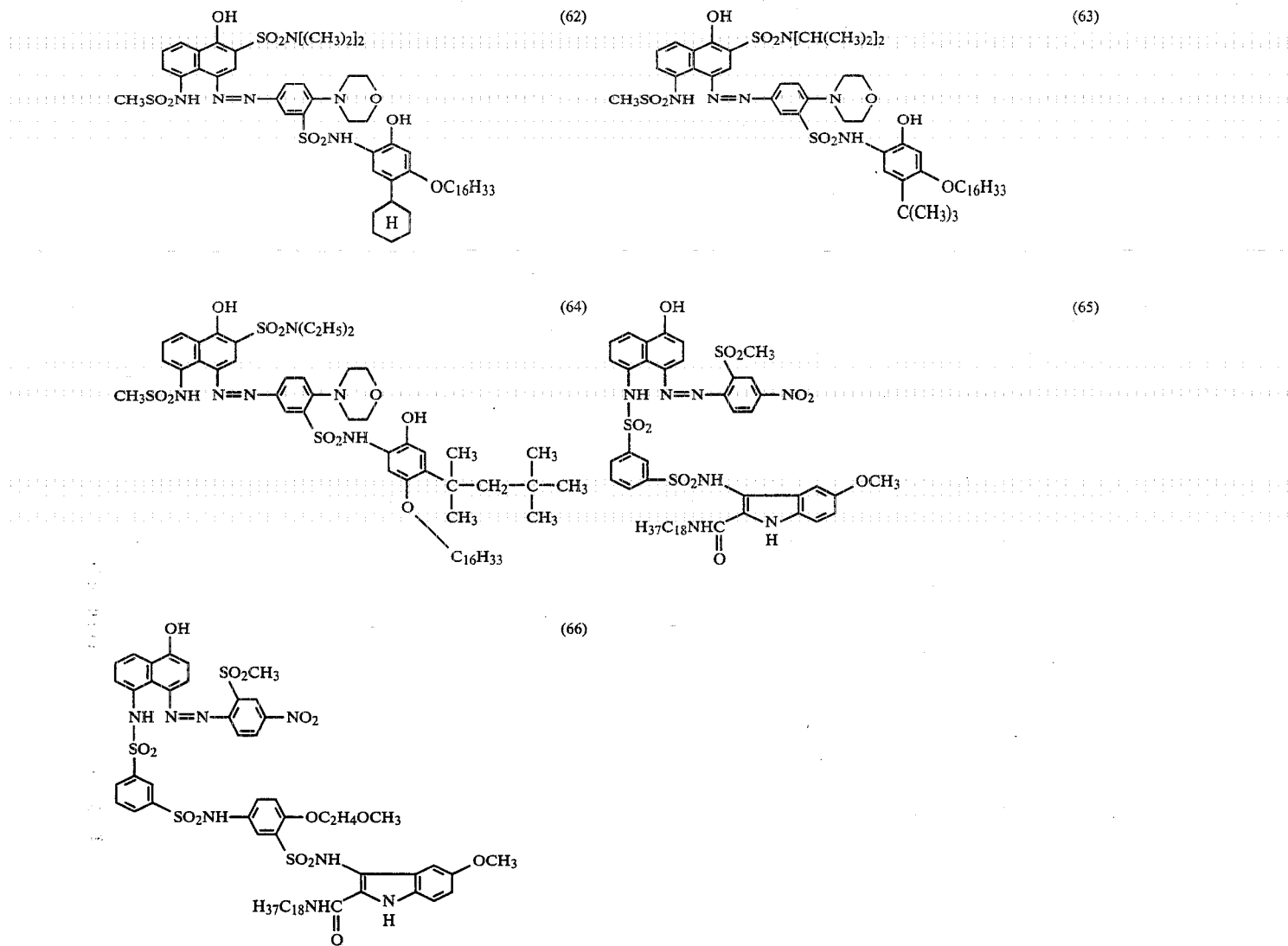

As the dye releasing redox compounds used in the present invention, the compounds as described, for example, in U.S. Pat. No. 4,055,428, Japanese Patent Application (OPI) Nos. 12642-81, 16130/81, 16131/81, 650/82 and 4043/82, U.S. Pat. Nos. 3,928,312 and 4,076,529, U.S. Published Patent Applicaton B 351,673, U.S. Pat. Nos. 4,135,929 and 4,198,235, Japanese Patent Application (OPI) No. 46730/78, U.S. Pat. Nos. 4,273,855, 4,149,892, 4,142,891 and 4,258,120, etc., are also effective in addition to the above described specific example.

Further, the dye releasing redox compounds which release a yellow dye as described, for example, in U.S. Pat. Nos. 4,013,633, 4,156,609, 4,148,641, 4,165,987, 4,148,643, 4,183,755, 4,246,414, 4,268,625 and 4,245,028, Japanese Patent Application (OPI) Nos. 71072/81, 25737/81, 138744/80, 134849/80, 106727/77, 114930/76, etc., can be effectively used in the present invention.

The dye releasing redox compounds which release a magenta dye as described, for example, in U.S. Pat. Nos. 3,954,476, 3,932,380, 3,931,144, 3,932,381, 4,268,624 and 4,255,509, Japanese Patent Application (OPI) Nos. 73057/81, 71060/81, 134850/80, 40402/80, 36804/80, 23628/78, 106726/77, 33142/80 and 53329/80, etc. can be effectively used in the present invention.

The dye releasing redox compounds which release a cyan dye as described, for example, in U.S. Pat. Nos. 3,929,760, 4,013,635, 3,942,987, 4,273,708, 4,148,642, 4,183,754, 4,147,544, 4,165,238, 4,246,414 and 4,268,625, Japanese Patent Application (OPI) Nos. 71061/81, 47823/78, 8827/77 and 143323/78, etc., can be effectively used in the present invention.

Processes for synthesizing the dye releasing redox compounds are described below.

Generally, the dye releasing redox compounds used in the present invention are obtained by condensing an amino group included in the reducing group R with a chlorosulfonyl group included in the image forming dye portion D.

The amino group of the reducing group R can be introduced by reduction of a nitro group, a nitroso group or an azo group or by ring-opening reaction of benzoxazoles and may be used as a free base or may be used as a salt of an inorganic acid. Further, the chlorosulfonyl group of the image forming dye portion D is obtained by converting the corresponding sulfonic acid or salts thereof using a chlorinating agent such as phosphorus oxychloride, phosphorus pentachloride or thionyl chloride, etc., according to a conventional method.

The condensation reaction of the reducing group R with the image forming dye portion D can be generally carried out in an aprotic polar solvent such as dimethylformamide, dimethylacetamide, dimethyl sulfoxide, N-methylpyrrolidone or acetonitrile, etc., in a presence of an organic base such as pyridine, picoline, lutidine, triethylamine or diisopropylethylamine, etc., at 0° to 50° C. by which the desired dye releasing redox compound can usually be obtained in a high yield. Synthesis examples of the dye releasing redox compounds are set forth below.

SYNTHESIS EXAMPLE 1

Synthesis of 6-Hydroxy-2-methylbenzoxazole

A mixture of 306 g of 2,4-dihydroxyacetophenone, 164 g of hydroxyamine hydrochloride, 328 g of sodium acetate, 1,000 ml of ethanol and 500 ml of water was refluxed by heating for 4 hours. The reaction solution was poured into 10 l of water to precipitate crystals and these crystals were collected by filtration. 314 g of 2,4-dihydroxyacetophenoneoxime was obtained.

30 g of the thus-obtained oxime was dissolved in 400 ml of acetic acid. While the acetic acid solution was heated at 120° C. with stirring, a hydrogen chloride gas was bubbled through the acetic acid solution for 2 hours. The acetic acid solution was cooled to precipitate crystals, and the crystals were collected by filtration and washed with water. 17 g of 6-hydroxy-2-methylbenzoxazole was obtained.

SYNTHESIS EXAMPLE 2

Synthesis of 6-Hexadecyloxy-2-methylbenzoxazole

A mixture of 18.0 g of 6-hydroxy-2-methylbenzoxazole obtained in Synthesis Example 1, 36.9 g of 1-bromohexadecane, 24.0 g of potassium carbonate and 120 ml of N,N-dimethylformamide was stirred at 90° C. for 4.5 hours. The reaction solution was filtered to remove solids and the filtrate was poured into 500 ml of ethanol to precipitate crystals. These crystals were collected by filtration. 45.0 g of 6-hexadecyloxy-2-methylbenzoxazole was obtained.

SYNTHESIS EXAMPLE 3

Synthesis of 2-Acetylamino-5-hexadecyloxyphenol

A mixture of 111 g of 6-hexadecyloxy-2-methylbenzoxazole obtained in Synthesis Example 2, 1,300 ml of ethanol, 110 ml of 33% hydrochloric acid and 550 ml of water was stirred at 55°–60° C. for 4 hours. The reaction solution was cooled to precipitate crystals, and the crystals were collected by filtration. 113 g of 2-acetylamino-5-hexadecyloxyphenol was obtained.

SYNTHESIS EXAMPLE 4

Synthesis of 2-Acetylamino-4-tert-butyl-5-hexadecyloxyphenol

A mixture of 30.0 g of 2-acetylamino-5-hexadecyloxyphenol obtained in Synthesis Example 3, 20.0 g of Amberlyst 15 (produced by Rohm & Haas, Co., U.S.A.) and 300 ml of toluene was stirred while heating at 80° to 90° C. during which isobutene was bubbled therethrough for 5 hours. The reaction solution was filtered to remove solids and the filtrate was condensed. On adding 350 ml of n-hexane to the residue, crystals precipitated. The crystals were collected by filtration. 23.5 g of 2-acetylamino-4-tert-butyl-5-hexadecyloxyphenol was obtained.

SYNTHESIS EXAMPLE 5

Synthesis of 2-Amino-4-tert-butyl-5-hexadecyloxyphenol

A mixture of 23.0 g of 2-acetylamino-4-tert-butyl-5-hexadecyloxphenol obtained in Synthesis Example 4, 120 ml of ethanol and 96 ml of 35% hydrochloric acid was refluxed with stirring for 5 hours. The reaction solution was cooled to precipitate crystals. The crystals were collected by filtration. 23.2 g of 2-amino-4-tert-butyl 5-hexacecyloxyphenol hydrochloride was obtained.

SYNTHESIS EXAMPLE 6

Synthesis of 4-tert-Butyl-5-hexadecyloxy-2-[2-(2-methoxyethoxy)-5-nitrobenzenesulfonylamino]phenol A mixture of 4.4 g of 2-amino-4-tert-butyl-5-hexadecyloxyphenol hydrochloride obtained in Synthesis Example 5 and 3.1 g of 2-(2-methoxyethoxy)-5-nitrobenzenesulfonyl chloride was dissolved in 12 ml of N,N-dimethylacetamide, to which 2,5 ml of pyridine was added. The resulting mixture was then stirred at 25° C. for 1 hour. On pouring the reaction solution into diluted hydrochloric acid, oily products precipitated. On adding 30 ml of methanol, the oily product crystallized. These crystals were collected by filtration. Yield: 4.5 g.

SYNTHESIS EXAMPLE 7

Synthesis of 2-[5-Amino-2-(2-methoxyethoxy)benzenesulfonylamino]-4-tert-butyl-5-hexadecyloxyphenol 10 g of the compound obtained in Synthesis Example 6 was dissolved in 60 ml of ethanol, and about 0.5 g of a 10% palladium-carbon catalyst was added. Thereafter, hydrogen was introduced at 55 kg/cm$^2$ and the above-prepared mixture was stirred at 60° C. for 6 hours. Then the catalyst was removed while the mixture was still hot, and the mixture was allowed to cool whereupon crystals precipitated. The crystals were collected by filtration. Thus, 7.5 g of 2-[5-amino-2-(2-methoxyethoxy)benzenesulfonylamino]-4-tert-butyl-5-hexadecyloxyphenol was obtained.

SYNTHESIS EXAMPLE 8

Synthesis of 3-Cyano-4-[4-(2-methoxyethoxy)-5-sulfophenylazo]-1-phenyl-5-pyrazolone To a solution prepared by dissolving 8.0 g of sodium hydroxide in 200 ml of water were added 49.4 g of 5-amino-2-(2-methoxyethoxy)benzenesulfonic acid and 50 ml of an aqueous solution of 13.8 g of sodium nitrite. Separately, a mixture of 60 ml of concentrated hydrochloric acid and 400 ml of water was prepared, to which was dropwise added at 5° C. or below the above-prepared solution. The resulting mixture was then stirred at 5° C. or below for 30 minutes to complete the reaction.

Separately, 16.0 g of sodium hydroxide, 200 ml of water, 33.0 g of sodium acetate and 200 ml of methanol were mixed to prepare a solution and 37.0 g of 3-cyano-1-phenyl-5-pyrazolone was added thereto. To the resulting solution the above-prepared diazo solution was dropwise added at 10° C. or below. After the dropwise addition was completed, the reaction mixture was stirred at 10° C. or below for 30 minutes and then at room temperature for 1 hour. The crystals precipitated were collected by filtration, washed with 200 ml of acetone and dried by air. Thus, 52.0 g of 3-cyano-4-[4-(2-methoxyethoxy)-5-sulfophenylazo]-1-phenyl-5-pyrazolone was obtained. m.p.: 263° to 265° C.

SYNTHESIS EXAMPLE 9

Synthesis for 3-Cyano-4-[4-(2-methoxyethoxy)-5-chlorosulfonylphenylazo]-1-phenyl-5-pyrazolone To a mixture of 51.0 g of 3-cyano-4-[4-(2-methoxyethoxy)-5-sulfophenylazo]-1-phenyl-5-pyrazolone obtained in Synthesis Example 8, 250 ml of acetone and 50 ml of phosphorus oxychloride was dropwise added 50 ml of N,N-dimethylacetamide at 50° C. or below. After the completion of the dropwise addition, the reaction mixture was stirred for about 1 hour and gradually poured into 1.0 l of ice water. The crystals precipitated were collected by filtration, washed with 100 ml of acetonitrile and dried by air. Thus, 46.7 g of 3-cyano-4-[4-(2-methoxyethoxy)-5-chlorosulfonylphenylazo]-1-phenyl-5-pyrazolone was obtained.
m.p.: 181° to 183° C.

SYNTHESIS EXAMPLE 10

Synthesis of Dye Releasing Redox Compound (1)

To a solution prepared by dissolving 6.3 g of 2-[5-amino-2-(2-methoxyethoxy)-benzenesulfonylamino]-4-tert-butyl-5-hexadecyloxyphenol obtained in Synthesis Example 7 in 30 ml of N,N-dimethylacetamide were added 4.6 g of 3-cyano-4-[4-(2-methoxyethoxy)-5-chlorosulfonylphenylazo]-1-phenyl-5-pyrazolone obtained in Synthesis Example 9 and furthermore 5 ml of pyridine. After stirring at room temperature for 1 hour, the reaction solution was poured into diluted hydrochloric acid. Precipitated crystals were collected by filtration and recrystallized from a solvent mixture of N,N-dimethylacetamide and methanol to obtain 7.5 g of Dye Releasing Redox Compound (1).
m.p.: 189° to 191° C.

SYNTHESIS EXAMPLE 11

Synthesis of Dye Releasing Redox Compound (2)

To a solution prepared by dissolving 6.3 g of 2-[5-amino-2-(2-methoxyethoxy)benzenesulfonylamino]-4-tert-butyl-5-hexadecyloxyphenol obtained in Synthesis Example 7 in 30 ml of N,N-dimethylacetamide were added 5.0 g of 3-cyano-4-(5-chloro-2-methylsulfonylphenylazo)-1-(4-chlorosulfonylphenyl)-5-pyrazolone and furthermore 5 ml of pyridine. After stirring at room temperature for 1 hour, the reaction solution was poured in diluted hydrochloric acid. Precipitated crystals were collected by filtration and recrystallized from acetonitrile to obtain 8.4 g of Dye Releasing Redox Compound (2).
m.p.: 144°–149° C.

SYNTHESIS EXAMPLE 12

Synthesis of Dye Releasing Redox Compound (10)

In 20 ml of N,N-dimethylacetamide were dissolved 4.4 g of 2-amino-4-tert-butyl-5-hexadecyloxyphenol hydrochloride and 6.5 g of 4-[3-chlorosulfonyl-4-(2-methoxyethoxy)phenylazo]-2-(N,N-diethylsulfamoyl)-5-methylsulfonylamino-1-naphthol, and 4.2 ml of pyridine was added thereto. After stirring at 25° C. for 1 hour, the reaction solution was poured into diluted hydrochloric acid. The solids thus precipitated were collected by filtration and purified by silica gel column chromatography (eluted by a chloroform-ethyl acetate (2:1) mixed solvent).
Yield: 5.2 g

SYNTHESIS EXAMPLE 13

Synthesis of Dye Releasing Redox Compound (17)

In 100 ml of N,N-dimethylacetamide was dissolved 11.6 g of 2-amino-4-tert-butyl-5-hexadecyloxyphenol hydrochloride, and 12 m of pyridine was added thereto. Then 20 g of 5-(3-chlorosulfonylbenzenesulfonylamino)-2-(N-tert-butylsulfamoyl)-4-(2-methylsulfonyl-4-nitrophenylazo)-1-naphthol was added. The resulting mixture was stirred for 1 hour and poured into 500 ml of ice water. The precipitates were collected and recrystallized from an isopropyl alcohol-acetonitrile (1:1) mixed solvent 6.8 g of Dye Releasing Redox Compound (17) was obtained.

SYNTHESIS EXAMPLE 14

Synthesis of Dye Releasing Redox Compound (19)

In 100 ml of N,N-dimethylacetamide were dissolved 31.5 g of 2-[5-amino-2-(2-methoxyethoxy)benzenesulfonylamino]-4-tert-butyl-5-hexadecyloxyphenyl and 39.1 g of 5-(3-chlorosulfonylbenzenesulfonylamino)-4-(2-methylsulfonyl-4-nitrophenylazo)-1-naphthol, and 21 ml of pyridine was added thereto. After the mixture was stirred for 80 minutes, 250 ml of methanol and 100 ml of water were added. A resinous product precipitated and solidified in a short time, and it was then collected by filtration. The crude product was recrystallized from a toluene-methanol-water (16:4:3) mixed solvent, thus 41.5 g of Dye Releasing Redox Compound (19) was obtained.

SYNTHESIS EXAMPLE 15

Synthesis of Dye Releasing Redox Compound (40)

(a) Synthesis of 2,5-Dihydroxy-4-tert-butylacetophenone 83 g of tert-butyl hydroquinone was dissolved in 400 ml of acetic acid and the solution was heated at 80° to 90° C. to which boron trifluoride was introduced for about 3 hours. After the completion of the reaction, the reaction mixture was poured into 1 liter of ice water and the viscous solid thus precipitated was collected by filtration. The solid was dissolved in 600 ml of a 2N sodium hydroxide solution and the insoluble material was removed by filtration. The filtrate was acidified with diluted hydrochloric acid, the crystals thus precipitated were collected by filtration, washed with water and recrystallized from water-containing methanol. Thus, 68 g (65% yield) of 2,5-dihydroxy-4-tert-butylacetophenone was obtained.

(b) Synthesis of 2,5-Dihydroxy-4-tert-butylacetophenone oxime 21 g of the ketone obtained in Step (a) above was dissolved by heating together with 70 ml of ethanol and 24 g of sodium acetate. To the solution was added with stirring a solution containing 12 g of hydroxylamine hydrochloride dissolved in 70 ml of water and the mixture was refluxed for about 1 hour. After the completion of the reaction, the reaction mixture was poured into 500 ml of ice water, the crystals thus precipitated were collected by filtration and recrystallized from a solvent mixture of benzene and hexane.

Yield: 17 g (76%)

(c) Synthesis of 6-tert-Butyl-5-hydroxy-2-methylbenzoxazole 14 g of the oxime obtained in Step (b) above was dissolved in 100 ml of acetic acid, to the solution a dry hydrogen chloride gas was introduced with heating and refluxed for 1.5 hours. After the completion of the reaction, the reaction mixture was poured into 500 ml of ice water, the crystals thus precipitated were collected by filtration and washed with water. Thus, 9 g (70% yield) of 6-tert-butyl-5-hydroxy-2-methylbenzoxazole was obtained.

(d) Synthesis of 6-tert-Butyl-5-hexadecyloxy-2-methylbenzoxazole 6.9 g of the benzoxazole derivative obtained in Step (c) above was dissolved in 50 ml of dimethylformamide and the solution was stirred at 80° to 90° C. for 6 hours together with 8 g of anhydrous potassium carbonate and 11 g of hexadecyl bromide. After the completion of the reaction, the insoluble material was removed by filtration. To the filtrate was added 150 ml of methanol and the mixture was cooled with ice to precipitate crystals. The crystals were collected by filtration, thus obtained 8.8 g (62%) yield) of 6-tert-butyl-5-hexadecyloxy-2-methylbenzoxazole.

(e) Synthesis of 2-Amino-5-tert-butyl-4-hexadecyloxyphenol hydrochloride 7.3 g of the benzoxazole compound obtained in Step (d) above was refluxed for 3 hours together with 30 ml of ethanol and 20 ml of concentrated hydrochloric acid. After the completion of the reaction, the reaction mixture was allowed to stand and cool. The crystals thus precipitated were collected by filtration, washed with water and then washed with acetone. Thus, 6.9 g (92% yield) of 2-amino-5-tert-butyl-4-hexadecyloxyphenol hydrochloride was obtained.

(f) Synthesis of Dye Releasing Redox Compound (40)

6 g of the hydrochloride obtained in Step (e) above and 8.8 g of sulfonyl chloride of dye having the structure shown below were dissolved in 50 ml of dimethylacetamide, to the solution was added 4 ml of pyridine and the mixture was stirred at room temperature for 1 hour. After the completion of the reaction, the reaction mixture was poured into diluted hydrochloric acid, the crystals thus precipitated were collected by filtration and washed with water. After drying, the product was purified by silica gel chromatography to obtain 2.2 g of Dye Releasing Redox Compound (40) as a substantially pure component.

Sulfonyl Chloride of Dye:

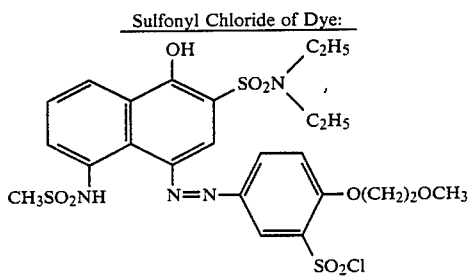

SYNTHESIS EXAMPLE 16

Synthesis of Dye Releasing Redox Compound (42)

In Step (d) of Synthesis Example 15 described above, O-hexadecylation was carried out using 6-tert-octyl-5-hydroxy-2-methylbenzoxazole in place of 6-tert-butyl-5-hydroxy-2-methylbenzoxazole. Then the same procedures as described in Step (e) and Step (f) of Synthesis Example 15 were repeated to obtain Dye Releasing Redox Compound (42).

The dye releasing redox compound which releases a diffusible dye according to the present invention can be used in an amount of a fixed range. Generally, a suitable range is about 0.01 mol to about 4 mols of the dye releasing redox compound per mol of the silver halide. A particularly suitable amount in the present invention is in a range of about 0.03 to about 1 mol per mol of the silver halide.

In the present invention, if necessary, a reducing agent may be used. The reducing agent in this case is the so-called auxiliary developing agent, which is oxidized by the silver salt oxidizing agent to form its oxidized product having an ability to oxidize the reducing group R in the dye releasing redox compound.

Examples of useful auxiliary developing agents include hydroquinone, alkyl substituted hydroquinones such as tertiary butyl hydroquinone or 2,5-dimethylhydroquinone,catechols, pyrogallols, halogen substituted hydroquinones such as chlorohydroquinone or dichlorohydroquinone, alkoxy substituted hydroquinones such as methoxyhydroquinone, and polyhydroxybenzene derivatives such as methyl hydroxynaphthalene, etc. Further, there are methyl gallate, ascorbic acid, ascorbic acid derivatives, hydroxylamines such as N,N-di(2-ethoxyethyl)-hydroxylamine, etc., pyrazolidones such as 1-phenyl-3-pyrazolidone or 4-methyl-4-hydroxymethyl-1-phenyl-3-pyrazolidone, etc., reductones and hydroxy tetronic acids.

The auxiliary developing agent can be used in an amount of a fixed range. A suitable range is 0.01 time by mol to 20 times by mol based on the silver halide. A particularly suitable range is 0.1 time by mol to 4 times by mol.

In the heat-developable color photographic material of the present invention, various kinds of bases or base releasing agents can be employed. By the use of the base or base releasing agent, a desirable color image can be obtained at a lower temperature.

Examples of preferred bases are amines which include trialkylamines, hydroxylamines, aliphatic polyamines, N-alkyl substituted aromatic amines, N-hydroxyalkyl substituted aromatic amines an bis[p-(dialkylamino))-phenyl]methanes. Further, there are betaine tetramethylammonium iodide and diaminobutane dihydrochloride as described in U.S. Pat. No. 2,410,644, and urea and organic compounds including amino acids such as 6-aminocaproic acid as described in U.S. Pat. No. 3,506,444. The base releasing agent is a compound or a mixture which releases a basic component by heating, and the basic component is capable of activating the photographic material. Examples of typical base releasing agents are described in British Pat. No. 998,949. A preferred base releasing agent is a salt of a carboxylic acid and an organic base, and examples of the suitable carboxylic acid include trichloroacetic acid and trifluoroacetic acid and examples of suitable base include guanidine, piperidine, morpholine, p-toluidine and 2-picoline, etc. Guanidine trichloroacetate as described in U.S. Pat. No. 3,220,846 is particularly preferred. Further, aldonic amides as described in Japanese Patent Application (OPI) No. 22625/75 are suitably used because they decompose at a high temperature to form a base.

Further, in the heat-developable color photographic material of the present invention many known compounds which activate development and simultaneously stabilize the images can be effectively used. Particularly, it is suitable to use isothiuroniums including 2-hydroxyethylisothiuronium trichloroacetate as described in U.S. Pat. No. 3,301,678, bisisothiuroniums including 1,8-(3,6-dioxaoctane)-bis(isothiuronium trifluoroacetate), etc., as described in U.S. Pat. No. 3,669,670, thiol compounds as described in West German Patent Application (OLS) No. 2,162,714, thiazolium compounds such as 2-amino-2-thiazolium trichloroacetate, 2-amino-S-bromoethyl-2-thiazolium trichloroacetate, etc., as described in U.S. Pat. No. 4,012,260, compounds having $\alpha$-sulfonylacetate as an acid part such as bis(2-amino-2-thiazolium)methylenebis(sulfonylacetate), 2-amino-2-thiazolium phenylsulfonylacetate, etc., as described in U.S. Pat. No. 4,060,420, and compounds having 2-carboxyamide as an acid part as described in U.S. Pat. No. 4,088,496.

These compounds or mixtures thereof can be used in a wide range of amounts. It is preferable to use them in a range of 1/100 to 10 times and particularly, 1/20 to 2 times by molar ratio based on silver.

The support used in the present invention is that which can endure at the processing temperature. Examples of useful supports include not only glass, paper, metal and analogues thereof, but also an acetyl cellulose film, a cellulose ester film, a polyvinyl acetal film, a polystyrene film, a polycarbonate film, a polyethylene terephthalate film and films related to them and a plastic material.

The photographic material according to the present invention may contain, if necessary, various additives known for the heat-developable photographic materials and may have a layer other than the light-sensitive layer, for example, an antistatic layer, an electrically conductive layer, a protective layer, an intermediate layer, an antihalation layer and a strippable layer, etc. Examples of additives include those described in *Research Disclosure*, Vol. 170, No. 17029 (June, 1978), for example, plasticizers, dyes for improving sharpness, antihalation dyes, sensitizing dyes, matting agents, surface active agents, fluorescent whitening agents and fading preventing agents, etc.

The protective layer, the intermediate layer, the subbing layer, the back layer and other layers can be produced by preparing each coating solution and applying to a support by various coating methods such as a dip coating method, an air-knife coating method, a curtain coating method or a hopper coating method as described in U.S. Pat. No. 3,681,294 and drying, likewise the case of the heat-developable photographic layer of the present invention, by which the photographic material is obtained.

If necessary, two or mor layers may be applied at the same time by the method as described in U.S. Pat. No. 2,761,791 and British Pat. No. 837,095.

For the heat-developable photographic material of the present invention, various means for exposing to light can be used. Latent images are obtained by imagewise exposure by radiant rays including visible rays. Generally, light sources used for conventional color prints can be used, examples of which include tungsten lamps, mercury lamps, halogen lamps such as an iodine lamp, a xenon lamp, laser light sources, CRT light sources, fluorescent tubes and light-emitting diodes, etc.

As the original, not only line drawings but also photographs having gradation may be used. Further, it is possible to take a photograph of a portrait or landscape by means of a camera. Printing from the original may be carried out by contact printing by superposing the original on the photographic material or may be carried out by reflection printing or enlargement printing.

It is also possible to carry out the printing of images photographed by a videocamera or image informations sent from a television broadcasting station by displaying on a cathode ray tube (CRT) or a fiber optical tube (FOT) and forcusing the resulting image on the heat-developable photographic material by contacting therewith or by means of a lens.

After the heat-developable color photographic material is exposed to light, the resulting latent image can be developed by heating the whole material to a suitably elevated temperature, for example, about 80° C. to about 250° C. for about 0.5 second to about 300 seconds. A higher temperature or lower temperature can be utilized to prolong or shorten the heating time, if it is within the above described temperature range. Particularly, a temperature range of about 110° C. to about 160° C. is useful. As the heating means, a simple heat plate, iron, heat roller or analogues thereof may be used.

In the present invention, a preferred specific method for forming a color image by heat development comprises heat diffusion transfer of a hydrophilic diffusible dye. For this purpose, the heat-developable color photographic material is composed of a support having thereon a light-sensitive layer (I) containing at least silver halide, an organic silver salt oxidizing agent, a dye releasing compound which is a reducing agent for the organic silver salt oxidizing agent and a hydrophilic binder, and an image receiving layer (II) capable of receiving the hydrophilic diffusible dye formed in the light-sensitive layer (I).

A dye releasing activator may be incorporated into the light-sensitive layer (I) or the image receiving layer (II). Alternatively, means for suppling the dye releasing activator, for example, a rupturable pod containing the dye releasing activator, a roller in which the dye releasing activator is immersed, an equipment which sprays a liquid containing the dye releasing activator, etc. may be provided separately.

The above described light-sensitive layer (I) and the image receiving layer (II) may be formed on the same support, or they may be formed on different supports, respectively. The image receiving layer (II) can be stripped off the light-sensitive layer (I). For example, after the heat-developable color photographic material is exposed imagewise to light, it is developed by heating uniformly and thereafter the image receiving layer (II) is peeled apart.

In accordance with another process, after the heat-developable color photographic material is exposed imagewise to light and developed by heating uniformly, the dye can be transferred on the image receiving layer (II) by superposing the image receiving layer on the light-sensitive layer (I) and heating to a temperature lower than the developing temperature. The temperature lower than the developing temperature in such a case includes room temperature and preferably a temperature from room temperature to a temperature not less than about 40° C. lower than the heat developing temperature. For example, a heat developing temperature and a transferring temperature are 120° C. and 80° C., respectively. Further, there is a method wherein only the light-sensitive layer (I) is exposed imagewise to light and then developed by heating uniformly by superposing the image receiving layer (II) on the light-sensitive layer (I).

The image receiving layer (II) can contain a dye mordant. In the present invention, various mordants can be used, and a useful mordant can be selected according to properties of the dye, conditions for transfer, and other components contained in the photographic material, etc. The mordants which can be used in the present invention include high molecular weight polymer mordants.

Polymer mordants to be used in the present invention are polymers containing secondary and tertiary amino groups, polymers containing nitrogen-containing heterocyclic moieties, polymers having quaternary cation groups thereof, having a molecular weight of from 5,000 to 200,000, and particularly from 10,000 to 50,000.

For example, there are illustrated vinylpyridine polymers and vinylpyridinium cation polymers as disclosed in U.S. Pat. Nos. 2,548,564, 2,484,430, 3,148,061 and 3,756,814, etc., polymer mordants capable of cross-linking with gelatin, etc., as disclosed in U.S. Pat. Nos. 3,625,694, 3,859,096 and 4,128,538, British Pat. No. 1,277,453, etc., aqueous sol type mordants as disclosed in U.S. Pat. Nos. 3,958,995, 3,721,852 and 2,798,063, Japanese Patent Application (OPI) Nos. 115228/79, 145529/79 and 126027/79, etc., water-insoluble mordants as disclosed in U.S. Pat. No. 3,898,088, etc., reactive mordants capable of forming covalent bonds with dyes used as disclosed in U.S. Pat. No. 4,168,976 (Japanese Patent Application (OPI) No. 137333/79), etc., and mordants disclosed in U.S. Pat. Nos. 3,709,690, 3,788,855, 3,642,482, 3,488,706, 3,557,066, 3,271,147 and 3,271,148, Japanese Patent Application (OPI) Nos. 71332/75, 30328/78, 155528/77, 125/78, and 1024/78, etc.

In addition, mordants disclosed in U.S. Pat. Nos. 2,675,316 and 2,882,156 can be used.

Of these mordants, those which migrate with difficulty from a mordanting layer to other layers are preferable; for example, mordants capable of cross-linking with a matrix such as gelatin, etc., water-insoluble mordants, and aqueous sol (or latex dispersion) type mordants are preferably used.

Particularly preferable polymer mordants are described below.

(1) Polymers having quaternary ammonium groups and groups capable of forming covalent bonds with gelatin (for example, aldehydo groups, chloroalkanoyl groups, chloroalkyl groups, vinylsulfonyl groups, pyridiniumpropionyl groups, vinylcarbonyl groups, alkylsulfonoxy groups, etc.), such as

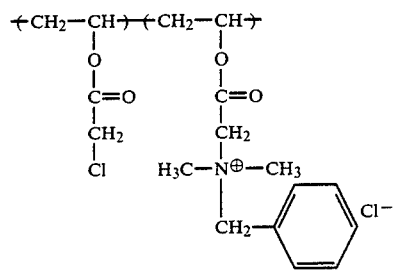

(2) Reaction products between a copolymer of a monomer represented by the following general formula with another ethylenically unsaturated monomer and a cross-linking agent (for example, bisalkanesulfonate, bisarenesulfonate, etc.):

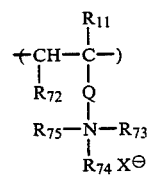

wherein $R_{71}$ represents H or an alkyl group $R_{72}$ represents H, an alkyl group or an aryl group, Q represents a divalent group, $R_{73}$, $R_{74}$ and $R_{75}$ each represents an alkyl group, an aryl group or at least two of $R_{73}$ to $R_{75}$ are bonded together to form a hetero ring, and X represents an anion. The above described alkyl groups and aryl groups may be substituted.

(3) Polymers represented by the following general formula

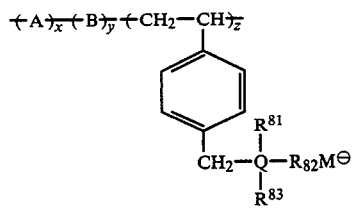

wherein x is from about 0.25 mol % to about 5 mol %, y is from about 0 mol % to about 90 mol %, z is from about 10 mol % to about 99 mol %, A represents a monomer having at least two ethylenically unsaturated bonds, B represents a copolymerizable ethylenically unsaturated monomer, Q represents N or P, $R_{81}$, $R_{82}$ and $R_{83}$ each represents an alkyl group or a cyclic hydrocarbon group or at least two of $R_{81}$ to $R_{83}$ are bonded together to form a ring (these groups and rings may be substituted), and M represents an anion.

(4) Copolymers composed of (a), (b) and (c), wherein (a) is

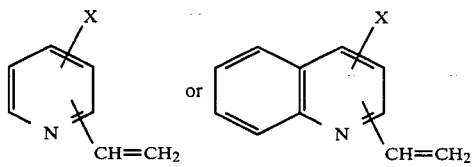

wherein X represents a hydrogen atom, an alkyl group or a halogen atom (the alkyl group may be substituted);
(b) is an acrylic acid ester; and
(c) is acrylonitrile.

(5) Water-insoluble polymers wherein at least ⅓ of the repeating units are those represented by the following general formula

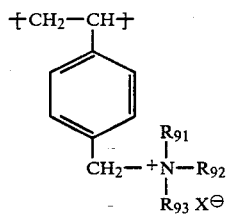

wherein $R_{91}$, $R_{92}$ and $R_{93}$ each represents an alkyl group, with the total number of carbon atoms being 12 or more (the alkyl group may be substituted), and X represents an anion.

(6) Polymers having the repeating unit represented by the following general formulae (d) and/or (e)

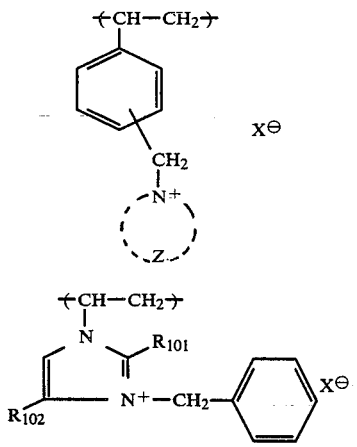

wherein Z represents atoms necessary to complete a nitrogen-containing hereto ring; $R_{101}$ and $R_{102}$ each represents H, an alkyl group, a hydroxyalkyl group or an aralkyl group; and X represents a monovalent anion.

Various known gelatins can be employed in the mordant layer. For example, gelatin which is produced in a different manner such as lime processed gelatin, acid processed gelatin, etc., or a gelatin derivative which is prepared by chemically modifying gelatin such as phthalated gelatin, sulfonylated gelatin, etc., can be used. Also, gelatin subjected to a desalting treatment can be used, if desired.

The ratio of polymer mordant to gelatin and the amount of the polymer mordant coated can be easily determined by one skilled in the art depending on the amount of the dye to be mordanted, the type and composition of the polymer mordant and further on the imageforming process used. Preferably, the ratio of mordant to gelatin is from about 20/80 to 80/20 (by weight) and the amount of the mordant coated is from 0.5 to 8 g/m².

The image receiving layer (II) can have a white-reflective layer. For example, a layer of titanium dioxide dispersed in gelatin can be provided on the mordant layer on a transparent support. The layer of titanium dioxide forms a white opaque layer, by which reflection color images of the transferred color images which is observed through the transparent support is obtained.

Typical image receiving materials for diffusion transfer are obtained by mixing the polymer containing ammonium salt groups which gelatin and applying the mixture to a transparent support.

The transfer of dyes from the photograhic layer to the image receiving layer can be carried out using a transfer solvent. Examples of useful transfer solvents include water and an alkaline aqueous solution containing sodium hydroxide, potassium hydroxide, an inorganic alkali metal salt, etc. Further, a solvent having a low boiling point such as methanol, N,N-dimethylformamide, acetone, diisobutyl ketone, etc., and a mixture of such a solvent having a low boiling point with water or an alkaline aqueous solution can be used. The transfer solvent can be employed by wetting the image receiving layer with the transfer solvent or by incorporating it in the form of water of crystallization or microcapsules into the photographic material.

The protective layer, the intermediate layer, the subbing layer, the back layer and other layers can be produced by preparing each coating solution and applying in order to the support by various coating methods such as a dip coating method, and air-knife coating method, a curtain coating method, a hopper coating method as described in U.S. Pat. No. 3,681,294 and drying to prepare the photographic material, in a manner similar to the heat-developable light-sensitive layer according to the present invention. If desired, two or more layers may be applied at the same time by the method as described in U.S. Pat. No. 2,761,791 and British Pat. 837,095.

The present invention will be explained in greater detail with reference to the following examples, but the present invention should not be construed as being limited thereto.

EXAMPLE 1

40 g of gelatin and 26 g of potassium bromide were dissolved in 3,000 ml of water and the solution was stirred while maintaining the temperature at 50° C. A solution containing 34 g of silver nitrate dissolved in 200 ml of water was added to the above described solution over a period of 10 minutes. Then, a solution containing 3.3 g of potassium iodide dissolved in 100 ml of water was added for a period of 2 minutes. By controlling the pH of the silver iodobromide emulsion thus prepared precipitate was formed and the excess salts were removed. The pH of the emulsion was then adjusted to 6.0 and 400 g of the silver iodobromide emulsion was obtained.

A mixture of 4 g of Dye Releasing Redox Compound (10), 8 g of Compound (14) according to the present invention and 30 ml of ethyl acetate was heated at about 60° C. to form a solution. The solution was mixed with 100 g of a 10% aqueous solution of gelatin and 10 ml of a 5% aqueous solution of sodium p-alkylsulfonate (alkyl groups of $C_{12}$ to $C_{13}$) and then dispersed using a homogenizer at 10,000 rpm for 10 minutes. The dispersion thus prepared is designated a dispersion using Compound (14) according to the present invention.

A comparative dispersion was prepared in the same manner as described above except using Comparative Compound (A) described below in place of Compound (14) according to the present invention.

COMPARATIVE COMPOUND (A)

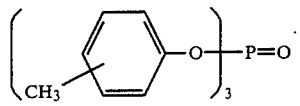

(mp. below −35° C.)

In the following, a method of preparing a light-sensitive coating is described.

| | | |
|---|---|---|
| (a) | a silver iodobromide emulsion | 25 g |
| (b) | a dispersion using Compound (14) according to the present invention | 33 g |
| (c) | a solution containing 1.5 g of guanidne trichloroacetate dissolved in 20 ml of ethanol | |
| (d) | a 5% aqueous solution of the following compound: $C_9H_{19}\text{−}\langle\rangle\text{−}O(CH_2CH_2O)_{\overline{5}}H$ | 10 ml |

The above-described components (a), (b), (c) and (d) were mixed and dissolved by heating. The solution was coated on a polyethylene terephthalate film at a wet thickness of 60 μm and dried. This sample was designated Sample (1).

Another sample was proposed in the same manner as described above except using the comparative dispersion in place of the dispersion using Compound (14) according to the present invention as the component (4). This sample was designated Sample (2).

In the following, a method of preparing an image receiving material having an image receiving layer is described.

10 g of copolymer of methyl acrylate and N,N,N-trimethyl-N-vinylbenzyl ammonium chloride (a ratio of methyl acrylate and vinylbenzyl ammonium chloride being 1:1) was dissolved in 200 ml of water and the solution was uniformly mixed with 100 g of a 10% aqueous solution of line process gelatin. The mixture solution was uniformly coated on a polyethylene terephthalate film at a wet thickness of 20 μm and dried to prepare an image receiving material. Samples (1) and (2) were exposed imagewise at 2,000 lux for 10 seconds using a tungsten lamp and then uniformly heated for 30 seconds on a heat block which had been heated at 130° C. Then, the image receiving material was soaked in water and superposed on the heated Samples (1) and (2) so as to bring into contact with each of the surface layers, and they were passed through a heat roller at 80° C. The image receiving material was peeled apart from Samples (1) and (2) thereby a negative magenta color image was obtained on the image receiving material. The maximum density (D max) and the miniumum density (D min) of the negative image to green light were measured using a Macbeth transmission densitometer (TD-504).

Further, Samples (1) and (2) was preserved in a container maintaining at 50° C. for 2 days, and then they were subjected to light exposure, heat-development and transfer in the same manner as described above.

The results thus obtained are shown in Table 1 below.

TABLE 1

| | Transmission Density of Color Image Transferred on Image Receiving Material | | | |
|---|---|---|---|---|
| | Just After Coating | | After Preservation at 50° C. for 2 Days | |
| Sample | D max | D min | D max | D min |
| (1) Present Invention | 1.11 | 0.12 | 1.22 | 0.40 |
| (2) Comparison | 1.14 | 0.17 | 1.49 | 1.29 |

It is apparent from the results shown in Table 1 that the occurrence of fog after the preservation is restrained and the change in the maximum density is minimized in the sample using the compound according to the present invention.

EXAMPLE 2

Dispersions were prepared in the same manner as described in Example 1 except using Dye Releasing Redox Compounds (33) and (19), respectively, in place of Dye Releasing Redox Compound (10) and coated to prepare samples. Further, comparative samples were prepared using a dispersion containing comparative Compound (B) described below.

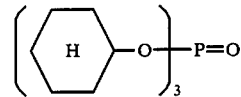

(mp. 60° C.)

These samples are designated Samples (3) to (6) as shown in Table 2 below.

TABLE 2

| Sample | Dye Releasing Redox Compound | Compound Used |
|---|---|---|
| (3) | (33) | Compound (14) of the present invention |
| (4) | (33) | Comparative Compound (B) |
| (5) | (19) | Compound (14) of the present invention |
| (6) | (19) | Comparative Compound (B) |

Samples (3) to (6) were subjected to light-exposure, heat-development and transfer in the same manner as described in Example 1. Transmission densities of these sample to blue light or red light were measured. The results obtained are shown in Table 3 below.

TABLE 3

| | Transmission Density of Color Image Transferred on Image Receiving Material | | | |
|---|---|---|---|---|
| | Just After Coating | | After Preservation at 50° C. for 2 Days | |
| Sample | D max | D min | D max | D min |
| (3) Present Invention | 0.62 | 0.15 | 0.64 | 0.26 |
| (4) Comparison | 0.64 | 0.19 | 0.71 | 0.39 |
| (5) Present Invention | 1.57 | 0.20 | 1.67 | 0.27 |

TABLE 3-continued

| | Transmission Density of Color Image Transferred on Image Receiving Material | | | |
|---|---|---|---|---|
| | Just After Coating | | After Preservation at 50° C. for 2 Days | |
| Sample | D max | D min | D max | D min |
| (6) Comparison | 1.62 | 0.22 | 1.87 | 0.50 |

It is apparent from the results shown in Table 3 that the occurrence of fog after the preservation is restrained by the addition of the compound according to the present invention, when Dye Releasing Redox Compounds (33) and (19) are used.

EXAMPLE 3

In the following, examples in which an organic silver salt oxidizing agent is used are described.

PREPARATION OF SILVER BENZOTRIAZOLE EMULSION 28 g of gelatin and 13.2 g of benzotriazole were dissolved in 3,000 ml of water and the solution was stirred while maintaining at 40° C. A solution containing 17 g of silver nitrate dissolved in 100 ml of water was added to the above described solution for a period of 2 minutes. By controlling a pH of the silver benzotriazole emulsion thus prepared to precipitate and the excess salts were removed. The pH of the emulsion was then adjusted to 6.0 and 400 g of the silver benzotrizole emulsion was obtained.

Using the silver benzotriazole emulsion thus prepared, a light-sensitive coating was prepared in the following manner.

| (a) | a silver iodobromide emulsion | 20 g |
|---|---|---|
| (b) | a silver benzotriazole emulsion | 10 g |
| (c) | a dispersion using the compound according to the present invention or the comparative compound as shown in Table 4 below (method for preparation was same as described in Example 1) | 33 g |
| (d) | a solution containing 1.5 g of guanidine trichloroacetate dissolved in 20 ml of ethanol | |
| (e) | a 5% aqueous solution of the following compound: | 10 ml |

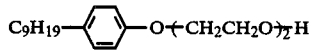

The above-described components (a), (b), (c), (d) and (e) were mixed and dissolved by heating. The solution was coated on a polyethylene terephthalate film at a wet thickness of 60 μm and dried. The samples thus prepared are designated Samples (7) to (12) as shown in Table 4 below.

TABLE 4

| Sample | Dye Releasing Redox Compound | Compound used in Dispersion (mp.) |
|---|---|---|
| (7) | (10) | ( —⟨H⟩—O)₃P=O    (60° C.) [Comparative Compound] |

TABLE 4-continued

| Sample | Dye Releasing Redox Compound | Compound used in Dispersion (mp.) |
|---|---|---|
| (8) | (10) | ⟨_⟩—COOCH₂—C(CH₃)₂—CH₂OCO—⟨_⟩ (49° C.) [Comparative Compound] |
| (9) | (10) | Compound (2)   (118–120° C.) [Present Invention] |
| (10) | (10) | Compound (2)   (71° C.) [Present Invention] |
| (11) | (10) | Compound (16)   (98° C.) [Present Invention] |
| (12) | (10) | Compound (9)   (120° C.) [Present Invention] |

Samples (7) to (12) were subjected to light-exposure, heat-development and transfer in the same manner as described in Example 1. Transmission densities of these samples to green light were measured. The results obtained are shown in Table 5 below.

TABLE 5

| | Transmission Density of Color Image Transferred on Image Receiving Material | | | |
|---|---|---|---|---|
| | Just After Coating | | After Preservation at 50° C. for 2 Days | |
| Sample | D max | D min | D max | D min |
| (7) Comparison | 1.45 | 0.24 | 1.80 | 1.57 |
| (8) Comparison | 1.23 | 0.20 | 1.64 | 1.39 |
| (9) Present Invention | 1.21 | 0.19 | 1.32 | 0.26 |
| 10 Present Invention | 1.33 | 0.21 | 1.57 | 0.34 |
| (11) Present Invention | 1.40 | 0.25 | 1.51 | 0.38 |
| (12) Present Invention | 1.39 | 0.27 | 1.46 | 0.42 |

It is apparent from the results shown in Table 5 that the occurrence of fog and the change in the maximum density after the preservation are restrained by using the compound according to the present invention.

While the invention has been described in detail and with reference to specific embodiment thereof, it will be apparent to one skilled in the art that various changes and modifications can be made therein without departing from the spirit and scope thereof.

What is claimed is:

1. A heat-developable color photographic material, comprising:
    a support having thereon;
    a light-sensitive silver halide;
    a hydrophilic binder;
    a dye releasing redox compound; and
    a heat fusible compound containing the dye releasing redox compound and dispersed in said hydrophilic binder, which heat fusible compound has a melting point of 60° C. or higher, the heat fusible compound being represented by a general formula selected from the group of general formulae consisting of (I), (II) and (III):

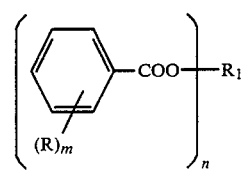   (I)

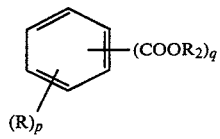   (II)

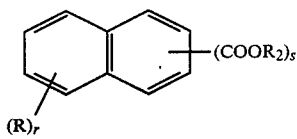   (III)

wherein m represents an integer from 1 to 3; n represents an integer from 1 to 8; q represents an integer from 1 to 4; p represents an integer which meets the requirement for p+q=6; s represents an integer from 1 to 4; r represents an integer which meets the requirement for r+s=8; R represents a hydrogen atom or a substituent selected from an alkyl group, a cycloalkyl group, an aryl group, an alkoxy group, an aryloxy group, an aralkyl group, an acyl group, an acylamino group, an alkylsulfonylamino group, an arylsulfonylamino group, an alkoxyalkyl group, an aryloxyalkyl group, an acyloxy group, an acyloxyalkyl group, a carbamoyl group, a N-substituted carbamoyl group, a ureido group, a N-substituted ureido group, an alkylamino group, a dialkyl amino group, an arylamino group, a halogen atom, a hydroxy group, a carboxy group, a nitro group, a cyano group, an alkoxycarbonyl group, an aryloxycarbonyl group and a cycloalkyloxycarbonyl group and the alkyl moiety, the cycloalkyl moiety and the aryl moiety of the substituents may be further substituted with a halogen atom, a hydroxy group, an alkoxy group, a cyano group, an aryloxy group, an alkyl group, an alkoxycarbonyl group or an aryloxycarbonyl group, and when m, p or r represents 2 or more, R may be the same or different; $R_1$ represents an organic group derived from a compound of the formula $R_1$—$(OH)_n$ which is derived from a compound represented by the following general formula (IV), (V) or (VI):

   (IV)

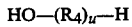   (V)

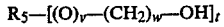   (VI)

wherein $R_3$ represents a t valent residue of an alkyl group, a substituted alkyl group, a cycloalkyl group or a substituted cycloalkyl group; $R_4$ represents an alkylene group or a substituted alkylene group; $R_5$ represents a t valent residue of an aryl group or a substituted aryl group; t represents an integer from 1 to 4; u represents an integer from 1 to 3; v represents 0 or an integer of 1; and w represents 0 or an integer from 1 to 3; wherein $R_2$ is a phenyl group, a substituted phenyl group, an alkyl group, a substituted alkyl group, a cycloalkyl group or a substituted cycloalkyl group.

2. A heat-developable color photographic material as claimed in claim 1, wherein the compound represented by the general formula (IV) is a compound represented by the following general formula (VII):

   (VII)

wherein $R_6$, $R_7$ and $R_8$, which may be the same or different, each represents a hydrogen atom, a hydroxy group, a hydroxymethyl group, or an alkyl group having from 1 to 4 carbon atoms; and $R_9$ represents a hydroxy group or a hydroxymethyl group.

3. A heat-developable color photographic material as claimed in claim 1, wherein a succharide represented by the general formula (V) is selected from the group consisting of glucose, arabinose, ribose, deoxyribose, xylose, furactose, mannose, galactose, succharose, lactose and maltose.

4. A heat-developable color photographic material as claimed in claim 1, wherein the heat fusible compound has a melting point in a range from 60° C. to 200° C.

5. A heat-developable color photographic material as claimed in claim 4, wherein the heat fusible compound has a melting point in a range from 60° C. to 150° C.

6. A heat-developable color photographic material as claimed in claim 1, wherein the heat fusible compound is present in a range from 0.05 times to 20 times by weight based on the dye releasing redox compound.

7. A heat-developable color photographic material as claimed in claim 1, wherein the light-sensitive silver halide is silver chloroiodide, silver iodobromide or silver chloroiodobromide each containing silver iodide crystal in its particle.

8. A heat-developable color photographic material as claimed in claim 1, wherein the dye releasing redox compound which is capable of releasing a hydrophilic diffusible dye is represented by the following general formula (X)

   (X)

wherein R represents a reducing group capable of being oxidized by the silver halide; and D represents a dye portion containing a hydrophilic group for forming an image.

9. A heat-developable color photographic material as claimed in claim 8, wherein the reducing group represented by R has an oxidation reduction potential to a saturated calomel electrode of 1.2 V or less.

10. A heat-developable color photographic material as claimed in claim 8, wherein the dye portion represented by D includes an azo dye, an azomethine dye, an anthraquinone dye, a naphthoquinone dye, a styryl dye, a nitro dye, a quinoline dye, a carbonyl dye or a phthalocyanine dye.

11. A heat-developable color photographic material as claimed in claim 1, wherein the color photographic material further comprises an image receiving layer capable of receiving the hydrophilic diffusible dye.

12. A heat-developable color photographic material as claimed in claim 1, wherein the color photographic material further contains a transfer solvent.

13. A method for forming a color image, comprising the steps of:

providing a heat-developable color photographic material comprising a support having thereon, a light-sensitive silver halide, a hydrophilic binder, a dye releasing redox compound and a heat fusible compound which has a melting point of 60° C. or higher, said heat fusible compound containing the dye releasing redox compound and dispersed in said hydrophilic binder, the heat fusible compound being represented by a general formula selected from the group of general formulae consisting of: (I), (II) and (III):

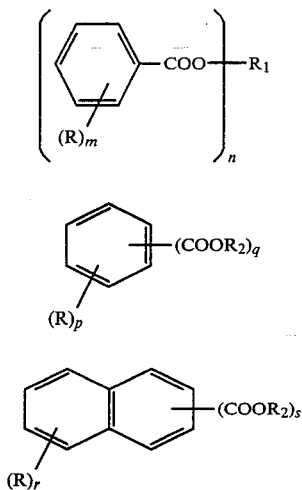

wherein m represents an integer from 1 to 3; n represents an integer from 1 to 8; q represents an integer from 1 to 4; p represents an integer which meets the requirement for p+q=6; s represents an integer from 1 to 4; r represents an integer which meets the requirement for r+s=8; R represents a hydrogen atom or a substituent selected from an alkyl group, a cycloalkyl group, an aryl group, an alkoxy group, an aryloxy group, an aralkyl group, an acyl group, an acylamino group, an alkylsulfonylamino group, an arylsulfonylamino group, an alkoxyalkyl group, an aryloxyalkyl group, an acyloxy group, an acyloxyalkyl group, a carbamoyl group, a N-substituted carbamoyl group, a ureido group, a N-substituted ureido group, an alkylamino group, a dialkylamino group, an arylamino group, a halogen atom, a hydroxy group, a carboxy group, a nitro group, a cyano group, an alkoxycarbonyl group, an aryloxycarbonyl group and a cycloalkyloxycarbonyl group and the alkyl moiety, the cycloalkyl moiety and the aryl moiety of the substituents may be further substituted with a halogen atom, a hydroxy group, an alkoxy group, a cyano group, an aryloxy group, an alkyl group, an alkoxycarbonyl group or an aryloxycarbonyl group, and when m, p or r represents 2 or more, R may be the same or different; $R_1$ represents an organic group derived from a compound of the formula $R_1$—$(OH)_n$ which is derived from a compound represented by the following general formula (IV), (V) or (VI):

$$R_3—(OH)_t \quad (IV)$$

$$HO—(R_4)_u—H \quad (V)$$

$$R_5—[(O)_v—(CH_2)_w—OH]_t \quad (VI)$$

wherein $R_3$ represents a t valent residue of an alkyl group, a substituted alkyl group, a cycloalkyl group or a substituted cycloalkyl group; $R_4$ represents an alkylene group or a substituted alkylene group; $R_5$ represents a t valent residue of an aryl group or a substituted aryl group; t represents an integer from 1 to 4; u represents an integer from 1 to 3; v represents 0 or an integer of 1; and w represents 0 or an integer from 1 to 3; wherein $R_2$ is a phenyl group, a substituted phenyl group, an alkyl group, a substituted alkyl group, a cycloalkyl group or a substituted cycloalkyl group;

imagewise exposing the heat-developable color photographic material;

developing the material by heating the material to a temperature in the range of 80° C. to 250° C. to release a hydrophilic diffusible dye; and transferring the diffusible dye onto an image receiving material.

14. A method of forming a color image as claimed in claim 13, wherein the transferring the diffusible dye is carried out by heating a temperature not less than 40° C. lower than the heat developing temperature.

15. A method of forming a color image as claimed in claim 13, wherein the transferring of the diffusible dye is carried out using a transfer solvent.

16. A heat-developable color photographic material as claimed in claim 1, wherein said fusible compound is present in a solid or near solid and non-fluid state and prevents the redox reaction between silver halide and the dye releasing redox compound or a subsequent dye releasing reaction before heat development but becomes fluid and acts as a medium for smoothly carrying out the redox reaction or the subsequent dye releasing reaction upon heating.

17. A heat-developable color photographic material as claimed in claim 1, which further comprises an image receiving layer capable of receiving a hydrophilic dye released by reaction between the dye releasing redox compound and the silver halide, which dye is imagewise released and transferred to the image receiving layer.

18. A method of forming a color image as claimed in claim 13, wherein the heat fusible compound is present in a solid or near solid and non-fluid state and prevents the redox reaction between silver halide and the dye releasing redox compound or a subseqent dye releasing reaction before heat development but becomes fluid and acts as a medium for smoothly carrying out the redox reaction or the subsequent dye releasing reaction upon heating.

19. A method of forming a color image as claimed in claim 13, wherein said heat-developable color photographic material further comprises an image receiving layer capable of receiving a hydrophilic dye released by reaction between the dye releasing redox compound and the silver halide, which dye is imagewise released and transferred to the image receiving layer.

* * * * *